US010729693B2

(12) United States Patent
Torres-Reveron et al.

(10) Patent No.: US 10,729,693 B2
(45) Date of Patent: Aug. 4, 2020

(54) COMPOSITIONS AND METHODS FOR THE TREATMENT OF ENDOMETRIOSIS

(71) Applicants: PONCE MEDICAL SCHOOL FOUNDATION, INC., Ponce, PR (US); The Board of Regents of the University of Texas System, Austin, TX (US)

(72) Inventors: Annelyn Torres-Reveron, Edinburg, TX (US); Caroline B. Appleyard, Ponce, PR (US); Idhaliz Flores, Ponce, PR (US)

(73) Assignees: PONCE MEDICAL SCHOOL FOUNDATION, INC., Ponce, PR (US); THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 16/288,820

(22) Filed: Feb. 28, 2019

(65) Prior Publication Data
US 2019/0269686 A1 Sep. 5, 2019

Related U.S. Application Data

(60) Provisional application No. 62/637,644, filed on Mar. 2, 2018.

(51) Int. Cl.
*C07D 487/04* (2006.01)
*A61K 31/519* (2006.01)
*A61P 15/00* (2006.01)
*A61K 31/505* (2006.01)

(52) U.S. Cl.
CPC .......... *A61K 31/519* (2013.01); *A61K 31/505* (2013.01); *A61P 15/00* (2018.01); *C07D 487/04* (2013.01)

(58) Field of Classification Search
CPC .................................................. C07D 487/04
See application file for complete search history.

(56) References Cited

U.S. PATENT DOCUMENTS

| | | | | |
|---|---|---|---|---|
| 5,795,905 A * | 8/1998 | McCarthy | ............ | C07D 239/42 514/383 |
| 6,211,195 B1 * | 4/2001 | Webb | ................... | C07D 495/04 514/217.07 |
| 6,218,397 B1 * | 4/2001 | Chen | ..................... | C07D 487/04 514/262.1 |
| 7,772,249 B2 * | 8/2010 | Hibi | ...................... | C07D 487/04 514/303 |
| 2002/0183375 A1 * | 12/2002 | Dubowchik | .......... | C07D 471/14 514/393 |
| 2003/0104087 A1 * | 6/2003 | Theoharides | .......... | A61K 31/13 424/769 |
| 2003/0220309 A1 * | 11/2003 | Monti | ................... | A61K 31/565 514/169 |
| 2005/0220912 A1 * | 10/2005 | Theoharides | ........ | A61K 31/138 424/771 |
| 2006/0058217 A1 * | 3/2006 | White | ................... | A61K 31/519 514/183 |
| 2006/0135417 A1 * | 6/2006 | Margioris | ............ | A61K 31/506 514/10.8 |
| 2008/0045610 A1 * | 2/2008 | Michalow | ............ | A61K 31/137 514/789 |
| 2009/0208939 A1 * | 8/2009 | Flores | ................. | C12Q 1/6883 435/6.12 |
| 2010/0069387 A1 | 3/2010 | Palmer et al. | | |
| 2019/0388413 A1 * | 12/2019 | Nanjundam | ....... | A61K 31/4709 |

FOREIGN PATENT DOCUMENTS

| | | | | |
|---|---|---|---|---|
| WO | WO 2004/064748 | | 8/2004 | |
| WO | WO-2007100775 A2 * | 9/2007 | ............. | A61K 31/00 |
| WO | WO-2009018169 A1 * | 2/2009 | ........... | C07C 215/64 |
| WO | WO-2009043468 A2 * | 4/2009 | ........... | A23C 9/1526 |

OTHER PUBLICATIONS

CAS Structure of CP-154526 (1994) (Year: 1994).*
D.W. Schulz et al., 93 Proc. Natl. Acad. Sci. USA, 10477-10482 (1996) (Year: 1996).*
P.J. Gilligan et al., 52 Journal of Medicinal Chemistry, 3084-3092 (2009) (Year: 2009).*
M.J. Owens et al., 43 Pharmaceutical Reviews (1991) (Year: 1991).*
A. Torres-Reveron et al., PLOS ONE (2018) (Year: 2018).*
E. Zoumakis et al., 155 European Journal of Endocrinology (2006) (Year: 2006).*
P. D. Kempuraj et al., 52 American Journal of Reproductive Immunology (2004) (Year: 2004).*
Carrarelli et al. "Urocortin and corticotrophin-releasing hormone receptor type 2 mRNA are highly expressed in deep infiltrating endometriotic lesions," Reprod. Biomed Online, 33(4):476-483 (2016).
Florio et al., "Paracrine regulation of endometrial function: interaction between progesterone and corticotropin-releasing factor (CRF) and activin A," Steroids, 68(10-13):801-7 (2003).
Florio et al., "Peritoneal fluid levels of immunoreactive corticotropin-releasing factor (CRF) and CRF-binding protein (CRF-BP) in healthy and endometriosic women," J. Endocrinol. Invest., 21(1):37-42 (1998).
Florio et al., "Plasma urocortin levels in the diagnosis of ovarian endometriosis," Obstet. Gynecol., 110(3):594-600 (2007).
Iavazzo et al., "The role of urocortin in gynecological and obstetrical conditions," Arch Gynecol Obstet., 279(5):613-9 (2009).
Kalantaridou et al., "The role of corticotropin-releasing hormone in blastocyst implantation and early fetal immunotolerance," Horm Metab Res., 39(6): 474-7 (2007).
Kalantaridou et al., "Reproductive functions of corticotropin-releasing hormone. Research and potential clinical utility of antalarmins (CRH receptor type 1 antagonists)," Am J Reprod Immunol., 51(4):269-74 (2004).

(Continued)

Primary Examiner — Alexander R Pagano
(74) Attorney, Agent, or Firm — Barnes & Thornburg LLP; Alice O. Martin

(57) ABSTRACT

The present disclosure provides methods for treating a mammal that has endometriosis using a CHRH1 antagonist composition. In some embodiments, the CHRH1 antagonist is antalarmin or an equivalent.

20 Claims, 15 Drawing Sheets

(56) References Cited

OTHER PUBLICATIONS

Kalantaridou et al., "Roles of reproductive corticotropin-releasing hormone," Ann N Y Acad Sci., 997:129-35 (2003).
Kempuraj et al., "Increased numbers of activated mast cells in endometriosis lesions positive for corticotropin-releasing hormone and urocortin," Am J Reprod Immunol., 52(4):267-75 (2004).
Makrigiannakis et al. "Endometrial and placental CRH as regulators of human embryo implantation," J Reprod Immunol., 62(1-2):53-9 (2004).
Makrigiannakis et al., "Endometrial CRH and implantation: from bench to bedside," Hormones (2018) 17:293-297.
Novembri et al., "Urocortin 2 and urocortin 3 in endometriosis: evidence for a possible role in inflammatory response," Mol Hum Reprod., 17(9):587-93 (2011).
Novembri et al., "Impaired CRH and Urocortin Expression and Function in Eutopic Endometrium of Women with Endometriosis," J. Clin. Endocrinol. Metab., 96(4): 1145-1150 (2011).
Pergialiotis et al., Urocortin Expression in Endometriosis: A Systematic Review, Int J Fertil Steril, 13(1): Apr.-Jun. 2019.
Search Report and Written Opinion issued in Int'l App. No. PCT/US2019/020017 (2019).
Tariverdian et al., "Neuroendocrine circuitry and endometriosis: progesterone derivative dampens corticotropin-releasing hormone-induced inflammation by peritoneal cells in vitro," J Mol Med (Berl), 88(3):267-78 (2010).
Torres-Reveron et al., "Antagonizing the corticotropin releasing hormone receptor 1 with antalarmin reduces the progression of endometriosis," PLOS ONE, 13(11): 1-25 (2018).
Torres-Reverón et al., Endometriosis Is Associated With a Shift in MU Opioid and NMDA Receptor Expression in the Brain Periaqueductal Gray. Reprod Sci. (2016) 23(9):1158-67.
Torres-Reveron et al., Hippocampal dynorphin immunoreactivity increases in response to gonadal steroids and is positioned for direct modulation by ovarian steroid receptors, Neuroscience. Mar. 3, 2009;159(1):204-16.
Torres-Reveron et al., Ovarian steroids modulate leu-enkephalin levels and target leuenkephalinergic profiles in the female hippocampal mossy fiber pathway. Brain Res. Sep. 26, 2008;1232:70-84.
Vergetaki et al., "Differential expression of CRH, UCN, CRHR1 and CRHR2 in eutopic and ectopic endometrium of women with endometriosis," PLoS One, 8(4):e62313 (2013).
Vergetaki et al., "Galectin-1 overexpression in endometriosis and its regulation by neuropeptides (CRH, UCN) indicating its important role in reproduction and inflammation," PLoS One, 4;9(12):e114229 (2014).
Vitoratos et al., "'Reproductive' Corticotropin-releasing hormone," Ann N Y Acad Sci., 1092: 310-318 (2006).
White et al., "Toxicity of Pexacerfont, a Corticotropin-Releasing Factor Type 1 Receptor Antagonist, in Rats and Dogs," Int. J Toxicol., Doi: 13:1091581819827501, 1-11 (2019).
Willenberg et al., "Effects of a novel corticotropin-releasing-hormone receptor type I antagonist on human adrenal function," Molecular Psychiatry (2000) 5, 137-141.
Zorrilla et al., "Effects of antalarmin, a CRF type 1 receptor antagonist, on anxiety-like behavior and motor activation in the rat," Brain Res., 18;952(2):188-99 (2002).
Zoumakis et al., "Chrotpicotropin releasing hormone receptor antagonists," Eur J Endocrinol., 155 S85-S91 (2006).

* cited by examiner

COMPOSITIONS AND METHODS FOR THE TREATMENT OF ENDOMETRIOSIS

CROSS REFERENCE TO RELATED APPLICATIONS

This application claims the benefit of priority under 35 U.S.C. § 119(e) to U.S. Provisional Patent Application No. 62/637,644, filed Mar. 2, 2018. The disclosure set forth in the referenced application is incorporated herein by reference in its entirety.

This invention was made with government support from the NIH NCCIH (National Center for Complementary and Integrated Health) Award No. K07 AT008027. The government has certain rights in the invention.

The present disclosure relates to the use of CRHR1 antagonists to competitively bind to Corticotropin releasing hormone receptors (CRHR1). More specifically, the disclosure provides compositions and methods for the treatment of endometriosis in a mammal using the antagonists.

BACKGROUND

Corticotropin releasing hormone (CRH) also referred to as corticotropin releasing factor (CRF) is one of the main signaling molecules of the hypothalamic pituitary adrenal (HPA) axis. CRH has a myriad of physiological effects that include behavioral, endocrine, autonomic and immune responses. CRH acts mainly by binding to CRH receptors type 1 (CRHR1) and type 2 (CRHR2) with a 10-fold affinity for the CRHR1 versus CRHR2. CRH receptors belong to the superfamily of G-protein coupled receptors and typically effect cellular activity via coupling to adenylate cyclase. CRHR1 is abundant in the brain, in adrenal glands, uterine and colonic tissues, and lymphocytes, for example. Eleven splice variants of the CRHR1 receptor have been identified, each with a tissue specific expression pattern. In addition, the naturally-produced CRH paralog, urocortin 1 (UCN1) can bind and activate both the CRHR1 and CRHR2. CRH is released in response to stress. CRH can affect nervous and visceral tissues such as the uterus and gut via activation of the two types of CRH receptors.

Due to the variety of physiological activities that the CRH system exerts, CRHR1 antagonists have been clinically used for more than three decades for a variety of conditions. For example, CRHR1 antagonists have been tested for the treatment of disorders including depression and irritable bowel syndrome (IBS). CRHR1 antagonists are proposed as a possible treatment for anxiety disorders. In fact, phase II/III clinical trials are ongoing or have been completed for depression, IBS and anxiety.

Antalarmin is a CRHR1 antagonist that has been investigated in animal research for its effects on reproduction, inflammation, addictive disorders, sleep disorders, among others. Antalarmin is a non-peptide molecule that readily crosses the blood-brain-barrier. Both anti-stress and anti-inflammatory activities of antalarmin have been documented in animal studies.

Endometriosis is a disorder in which endometrial tissue is found outside the uterus causing pain, infertility and stress. Finding an effective and long-term treatment for endometriosis still remains one of the most significant challenges in the field of obstetrics and gynecology.

Endometriosis is a chronic inflammatory disorder defined as the presence of endometrial-like tissue (e.g., glands and stroma) outside the endometrial cavity. This condition is characterized by peritoneal inflammation resulting in severe and chronic pelvic pain, and increases risk of infertility. Endometriosis is commonly misdiagnosed as irritable bowel syndrome (IBS) due to overlap in common symptoms, and perhaps because mechanisms of disease progression involve aberrant activation of inflammatory cascades. The causes of endometriosis onset are unknown; however, a relationship between stress, hypothalamic pituitary adrenal axis (HPA) dysregulation, and endometriosis severity has been reported based on investigations in a rat model.

Reports from human and animal studies, suggest that abnormal functioning of the HPA axis, and the release of CRH and/or the inflammatory response system, disrupts feedback of both neuroendocrine and immune systems, contributing to the development of endometriosis. Indeed, CRH and CRH receptors are abundant in female reproductive tissues. This axis has been shown to regulate several reproductive functions, mostly mediating pro-inflammatory activities such as ovulation, luteolysis, and blastocyst implantation. Despite the documented role of CRH receptors in stress related disorders, reproductive function, and inflammation, a role of the CRHR1 blockade in the treatment of endometriosis, is not established.

SUMMARY

CRH is one of the main signaling peptides within the hypothalamic pituitary adrenal axis released in response to stress. CRH can affect nervous and visceral tissues such as the uterus and gut via activation of two types of CRH receptors: CRHR1 and CRHR2. Methods of treatment for endometriosis are disclosed using CRHR1 antagonists.

The present disclosure provides methods for treating a mammal that has endometriosis by administering an effective amount of CRHR1 antagonist. In an embodiment, a mammal, including a human, diagnosed with endometriosis is provided an effective amount of CRHR1 antagonist. In another embodiment, the CRHR1 antagonist is antalarmin.

A well-established auto transplantation rat model of endometriosis was used to investigate the effects of the CRHR1 antagonist antalarmin in endometriosis. Given the role of CRHR1 in inflammation, the disclosure first shows the extent to which the receptor was up regulated in ectopically implanted endometrium shortly after disease (endometriosis) induction. Following this, antalarmin was administered early during endometriosis establishment to test whether the antagonist could block vesicle formation in this model.

The results of the blockade of CRHR1 during the first week after endometriosis induction were observed. The initiation of inflammatory processes that lead to endometriosis vesicle establishment and subsequent development, was reduced. Further, CRHR1 blockades at certain levels reduced stress associated behaviors previously linked to endometriosis, such as anxiety and depression. Treatment with antalarmin significantly reduced the size (67% decrease) and number (30% decrease) of endometriotic vesicles. Antalarmin also prevented the increase in CRH and CRHR1 mRNA within endometriotic vesicles, but not of glucocorticoid receptor. Endometriosis did not change anxiety behaviors in the open field and zero-maze tests and prior antalarmin administration did not modify this. Data presented herein shows that the CRHR1 antagonist antalarmin functions as a completely new line of treatment for women suffering from endometriosis. This treatment is highly needed in the management of this debilitating and still incurable disease.

The following numbered embodiments are contemplated and are non-limiting:

1. A method of treating endometriosis in a mammal in need thereof, said method comprising the step of administering a pharmaceutical composition comprising a corticotrophin releasing hormone (CRH) receptor antagonist to the mammal.
2. The method of clause 1, wherein the CRH receptor antagonist is a CRH1 receptor antagonist.
3. The method of clause 2, wherein the CRH1 receptor antagonist is selected from the group consisting of LWH-234, CP-154,526, NBI-27914, R-121,919, verucerfont (GSK-561679), GW-876008, pexacerfont (BMS-562,086), CRA-1000, and NBI-35965.
4. The method of clause 2, wherein the CRH1 receptor antagonist is LWH-234.
5. The method of clause 2, wherein the CRH1 receptor antagonist is CP-154,526.
6. The method of clause 2, wherein the CRH1 receptor antagonist is NBI-27914.
7. The method of clause 2, wherein the CRH1 receptor antagonist is R-121,919.
8. The method of clause 2, wherein the CRH1 receptor antagonist is verucerfont (GSK-561679).
9. The method of clause 2, wherein the CRH1 receptor antagonist is GW-876008.
10. The method of clause 2, wherein the CRH1 receptor antagonist is pexacerfont (BMS-562,086).
11. The method of clause 2, wherein the CRH1 receptor antagonist is CRA-1000.
12. The method of clause 2, wherein the CRH1 receptor antagonist is NBI-35965.
13. The method of clause 1, wherein the CRH receptor antagonist is a CRH2 receptor antagonist.
14. The method of clause 13, wherein the CRH2 receptor antagonist is astressin-B or α-helical CRF 9-41.
15. The method of clause 13, wherein the CRH2 receptor antagonist is astressin-B.
16. The method of clause 13, wherein the CRH2 receptor antagonist is α-helical CRF 9-41.
17. The method of clause 1, wherein the CRH receptor antagonist is antalarmin.
18. The method of any one of clauses 1 to 17, wherein the pharmaceutical composition further comprises a second CRH receptor antagonist.
19. The method of clause 18, wherein the second CRH receptor antagonist is a CRH1 receptor antagonist.
20. The method of clause 19, wherein the CRH1 receptor antagonist is selected from the group consisting of LWH-234, CP-154,526, NBI-27914, R-121,919, verucerfont (GSK-561679), GW-876008, pexacerfont (BMS-562,086), CRA-1000, and NBI-35965.
21. The method of clause 19, wherein the CRH1 receptor antagonist is LWH-234.
22. The method of clause 19, wherein the CRH1 receptor antagonist is CP-154,526.
23. The method of clause 19, wherein the CRH1 receptor antagonist is NBI-27914.
24. The method of clause 19, wherein the CRH1 receptor antagonist is R-121,919.
25. The method of clause 19, wherein the CRH1 receptor antagonist is verucerfont (GSK-561679).
26. The method of clause 19, wherein the CRH1 receptor antagonist is GW-876008.
27. The method of clause 19, wherein the CRH1 receptor antagonist is pexacerfont (BMS-562,086).
28. The method of clause 19, wherein the CRH1 receptor antagonist is CRA-1000.
29. The method of clause 19, wherein the CRH1 receptor antagonist is NBI-35965.
30. The method of clause 18, wherein the second CRH receptor antagonist is a CRH2 receptor antagonist.
31. The method of clause 30, wherein the CRH2 receptor antagonist is astressin-B or α-helical CRF 9-41.
32. The method of clause 30, wherein the CRH2 receptor antagonist is astressin-B.
33. The method of clause 30, wherein the CRH2 receptor antagonist is α-helical CRF 9-41.
34. The method of clause 18, wherein the second CRH receptor antagonist is antalarmin.
35. The method of any one of clauses 1 to 34, wherein the pharmaceutical composition further comprises one or more agents selected from the group consisting of a surfactant, a stabilizer, a biomarker, a second active pharmaceutical ingredient (API), and combinations thereof.
36. The method of any one of clauses 1 to 35, wherein the pharmaceutical composition further comprises at least one excipient, a bioavailability-improving compound, at least one coating, or a combination thereof.
37. The method of any one of clauses 1 to 36, wherein administration is at a dose of about 0.001 to about 1000 mg of CRH receptor antagonist per kg of mammal body weight.
38. The method of any one of clauses 1 to 36, wherein administration is at a dose of about 0.001 to about 100 mg of CRH receptor antagonist per kg of mammal body weight.
39. The method of any one of clauses 1 to 36, wherein administration is at a dose of about 0.01 to about 100 mg of CRH receptor antagonist per kg of mammal body weight.
40. The method of any one of clauses 1 to 36, wherein administration is at a dose of about 0.1 to about 100 mg of CRH receptor antagonist per kg of mammal body weight.
41. The method of any one of clauses 1 to 36, wherein administration is at a dose of about 0.1 to about 10 mg of CRH receptor antagonist per kg of mammal body weight.
42. The method of any one of clauses 1 to 36, wherein administration is at a dose of about 1 to about 5 mg of CRH receptor antagonist per kg of mammal body weight.
43. The method of any one of clauses 1 to 36, wherein administration is at a dose of about 1 mg of CRH receptor antagonist per kg of mammal body weight.
44. The method of any one of clauses 1 to 36, wherein administration is at a dose of about 2 mg of CRH receptor antagonist per kg of mammal body weight.
45. The method of any one of clauses 1 to 36, wherein administration is at a dose of about 3 mg of CRH receptor antagonist per kg of mammal body weight.
46. The method of any one of clauses 1 to 36, wherein administration is at a dose of about 4 mg of CRH receptor antagonist per kg of mammal body weight.
47. The method of any one of clauses 1 to 36, wherein administration is at a dose of about 5 mg of CRH receptor antagonist per kg of mammal body weight.
48. The method of any one of clauses 1 to 47, wherein the administration is a parenteral administration.
49. The method of clause 48, wherein the parenteral administration is an intravenous administration.
50. The method of clause 48, wherein the parenteral administration is an intramuscular administration.

51. The method of clause 48, wherein the parenteral administration is a subcutaneous administration.
52. The method of any one of clauses 1 to 47, wherein the administration is an oral administration.
53. The method of any one of clauses 1 to 52, wherein the administration is a single dose administration.
54. The method of any one of clauses 1 to 59, wherein the administration is a single unit dose administration.
55. The method of any one of clauses 1 to 54, wherein the mammal is a human
56. The method of any one of clauses 1 to 55, wherein the administration is given to the mammal for 7 days.
57. The method of any one of clauses 1 to 55, wherein the administration is given to the mammal for 14 days.
58. The method of any one of clauses 1 to 55, wherein the administration is given to the mammal for 21 days.
59. The method of any one of clauses 1 to 55, wherein the administration is given to the mammal for 28 days.
60. The method of any one of clauses 1 to 55, wherein the administration is given to the mammal once per day.
61. The method of any one of clauses 1 to 55, wherein the administration is given to the mammal once every 48 hours.
62. The method of any one of clauses 1 to 55, wherein the administration is given to the mammal once every 72 hours.
63. The method of any one of clauses 1 to 55, wherein the administration is given to the mammal once every 96 hours.
64. The method of any one of clauses 1 to 55, wherein the administration is given to the mammal once every week.
65. The method of any one of clauses 1 to 55, wherein the administration is given to the mammal once every 2 weeks.
66. The method of any one of clauses 1 to 55, wherein the administration is given to the mammal once every 3 weeks.
67. The method of any one of clauses 1 to 55, wherein the administration is given to the mammal once every 4 weeks.
68. The method of any one of clauses 1 to 55, wherein the administration is given to the mammal once every 6 weeks.
69. The method of any one of clauses 1 to 55, wherein the administration is given to the mammal once every month.
70. The method of any one of clauses 1 to 55, wherein the administration is given to the mammal once every 2 months.
71. The method of any one of clauses 1 to 55, wherein the administration is given to the mammal once every 3 months.
72. A method of treating a symptom associated with endometriosis in a mammal in need thereof, said method comprising the step of administering a corticotrophin releasing hormone (CRH) receptor antagonist to the mammal.
73. The method of clause 72, wherein the symptom associated with endometriosis is selected from the group consisting of lesion formation, lesion enlargement, pain, infertility, inflammation, depression, anxiety, and stress.
74. The method of clause 72, wherein the symptom associated with endometriosis is lesion formation.
75. The method of clause 74, wherein the lesion formation is an endometriotic vesicle formation.
76. The method of clause 74, wherein the lesion formation is a cyst formation.
77. The method of clause 72, wherein the symptom associated with endometriosis is lesion enlargement.
78. The method of clause 72, wherein the symptom associated with endometriosis is pain.
79. The method of clause 72, wherein the symptom associated with endometriosis is infertility.
80. The method of clause 72, wherein the symptom associated with endometriosis is inflammation.
81. The method of clause 72, wherein the symptom associated with endometriosis is depression.
82. The method of clause 72, wherein the symptom associated with endometriosis is anxiety.
83. The method of clause 72, wherein the symptom associated with endometriosis is stress.
84. The method of clause 72, wherein the method controls the symptom associated with endometriosis in the mammal.
85. The method of clause 72, wherein the method reduces the symptom associated with endometriosis in the mammal.
86. The method of any one of clauses 72 to 85, wherein the method comprises an embodiment of any one of clauses 1 to 71.
87. A method of treating inflammation associated with endometriosis in a mammal in need thereof, said method comprising the step of administering a corticotrophin releasing hormone (CRH) receptor antagonist to the mammal.
88. The method of clause 87, wherein the method reduces an amount of an inflammatory cytokine in the mammal.
89. The method of clause 88, wherein the inflammatory cytokine is an interleukin.
90. The method of clause 89, wherein the interleukin is IL-6.
91. The method of clause 88, wherein the inflammatory cytokine is TNF-α.
92. The method of any one of clauses 87 to 91, wherein the method comprises an embodiment of any one of clauses 1 to 71.
93. A method of treating stress associated with endometriosis in a mammal in need thereof, said method comprising the step of administering a corticotrophin releasing hormone (CRH) receptor antagonist to the mammal.
94. The method of clause 93, wherein the method reduces an amount of corticosterone in the mammal.
95. The method of clause 93, wherein the method reduces an amount of adrenocorticotropic hormone (ACTH) in the mammal.
96. The method of any one of clauses 93 to 95, wherein the method comprises an embodiment of any one of clauses 1 to 71.
97. A method of reducing lesion formation or lesion enlargement associated with endometriosis in a mammal in need thereof, said method comprising the step of administering a corticotrophin releasing hormone (CRH) receptor antagonist to the mammal.
98. The method of clause 97, wherein the lesion is an endometriotic vesicle.
99. The method of clause 97, wherein the lesion is a cyst.
100. The method of clause 99, wherein the cyst is an ovarian cyst.
101. The method of any one of clauses 97 to 100, wherein the method reduces the number of lesion sites in the mammal.
102. The method of any one of clauses 97 to 100, wherein the method reduces the size of one or more lesions in the mammal.

103. The method of any one of clauses 97 to 102, wherein the method comprises an embodiment of any one of clauses 1 to 71.
104. A method of reducing a marker of endometriosis in a mammal brain, said method comprising the step of administering a corticotrophin releasing hormone (CRH) receptor antagonist to the mammal.
105. The method of clause 104, wherein the marker of endometriosis is mRNA.
106. The method of clause 105, wherein the mRNA is CRHR1 mRNA.
107. The method of clause 105, wherein the mRNA is corticotrophin releasing hormone receptor type 1 (CRHR1) mRNA.
108. The method of clause 105, wherein the mRNA is corticotrophin releasing hormone receptor type 2 (CRHR2) mRNA.
109. The method of clause 105, wherein the mRNA is corticotrophin releasing hormone (CRH) mRNA.
110. The method of clause 105, wherein the mRNA is glucocorticoid receptor (GR) mRNA.
111. The method of clause 104, wherein the marker of endometriosis is a peptide or a protein.
112. The method of clause 111, wherein the peptide is corticotrophin releasing hormone (CRH) peptide.
113. The method of clause 111, wherein the peptide is corticotrophin releasing hormone (CRH) urocortin.
114. The method of clause 111, wherein the protein is corticotrophin releasing hormone receptor type 1 (CRHR1).
115. The method of clause 111, wherein the protein is glucocorticoid receptor (GR).
116. The method of any one of clauses 104 to 115, wherein the marker of endometriosis is located in the hippocampus of the mammal brain.
117. The method of any one of clauses 104 to 116, wherein the method comprises an embodiment of any one of clauses 1 to 71.

BRIEF DESCRIPTION OF THE DRAWINGS

(FIG. 4A) The percent of implants that developed into vesicles was significantly lower in the antalarmin treated group compared to the vehicle control group; (FIG. 4B) The total weight of all vesicles per rat was smaller for the antalarmin treated rats; (FIG. 4C) The average vesicle volume per rat was significantly smaller for the antalarmin treated group compared to the vehicle control group; (FIG. 4D) The average vesicle area per rat was significantly smaller in the antalarmin group compared to the vehicle group; (FIG. 4E) Vesicles that developed were classified by grade based on a scale by size. * $p<0.05$, ** $p<0.01$.

(FIG. 6A) corticotropin releasing hormone (CRH); (FIG. 6B) Urocortin 1 peptide. (Data were normalized to the uterus of sham rats. * represents $p<0.05$ compared to sham rats' uterus.)

(FIG. 7A) corticotropin releasing hormone receptor type 1 (CRHR1); (FIG. 7B) corticotropin releasing hormone receptor type 2 (CRHR2); (FIG. 7C) glucocorticoid receptor (GR). (Data was normalized to the uterus of sham (control) rats. * represents $p<0.05$ compared to sham rats' uterus.)

(FIG. 8B) During the subsequent weeks, the antalarmin group remained weighing less than the control group and by weeks 6 and 7 this difference reached statistical significance. * $p<0.05$, ** $p<0.01$.

(FIG. 10A) Corticotropin releasing hormone receptor type 1 (CRHR1), (FIG. 10B) corticotropin releasing hormone receptor type 2 (CRHR2), (FIG. 10C) corticotropin releasing hormone (CRH) (FIG. 10D) glucocorticoid receptor (GR). Data normalized to the mRNA of sham rats. * represents $p<0.05$ compared to sham rats hippocampus. (FIG. 10E) diagram of the dorsal hippocampus. Whole hippocampus was used for measuring the mRNA.

(FIG. 11A) Diagram of the paraventricular nucleus (PVN) of the hypothalamus, the main nuclei expressing CRH in this region. (FIG. 11B) Diagram of the dorsal hippocampus showing the areas from where measurements were taken as indicated by arrows. (FIG. 11C) Graphical representation of CRH immunolabeling in the PVN (FIG. 11D) Graphical representation of immunolabeling in the CA3# region of the hippocampus. No changes in CRH peptide were measured in either the PVN or hippocampus.

(FIG. 12A) Diagram of the dorsal hippocampus showing the areas from where measurements were taken as indicated by arrows. (FIG. 12B) Graphical representation of CRHR1 immunolabeling in the dentate gyrus (DG) (FIGS. 12C-12D) Graphical representation of immunolabeling in the CA3b and CA3a regions of the hippocampus. Large increases in CRHR1 labeling were observed for both groups with endometriosis in the DG, regardless of treatment. No changes in CRHR1 were observed in either the CA3. ** $p<0.01$ compared to sham.

(FIG. 13A) Diagram of the dorsal hippocampus showing the areas from where measurements were taken as indicated by arrows. (FIG. 13B) Graphical representation of GR immunolabeling in the dentate gyrus (DG) (FIG. 13C) Graphical representation of immunolabeling in the CA3a region of the hippocampus. Large increases in GR labeling were observed for both groups with endometriosis in the DG, regardless of treatment. However, no changes in GR were observed in either the CA3. *** $p<0.001$ compared to sham (FIG. 14A) The number of rats that were at each stage of the estrous cycle the day of behavioral testing and sacrifice for experiment 1. Estrous cycle before endometriosis surgery was not assessed in these rats. (FIG. 14B) Estrous cycle in rats for experiment 2 was assessed for 10 days prior to induction surgery. The percent of time that each experimental group spent in each of the phases of the estrous cycle. (FIG. 14C) The number of rats that were on each phase of the estrous cycle on the day of behavioral testing and sacrifice, 60 days after the induction surgery. Note that one rat in the sham group had irregular cycles and was removed from the group.

(FIGS. 15A and 15B) Total distance traveled in the open field and time spent in the center. (FIG. 15C and FIG. 15D) Total distance traveled in the zero maze and time spent in the open arms of the maze. Parametric analyses were not performed due to the small number of animals in each estrous cycle group. Numbers at the bottom of bars in panel A represent the number of animals per group per stage of estrous cycle. Bars represent mean±S.E.M. in this and all subsequent supplemental figures.

(FIG. 16A and FIG. 16B) Total distance traveled in the open field and time spent in the center. (FIG. 16C and FIG. 16D) Total distance traveled in the zero maze and time spent in the open arms of the maze Table 2 illustrates the statistical results of the Two-way ANOVAs for each panel showing no effects of estrous cycle. Numbers at the bottom of bars in panel A represent the number of animals per group per stage of estrous cycle. It should be noted that the number of animals per group in the diestrus stage of the estrous cycle was small.

(FIG. 17A) Percent developed vesicles. (FIG. 17B) Group means of the total vesicle weight per rat. (FIG. 17C) Group means for the total vesicle volume per rat. (FIG. 17D) Group means for the total vesicle area per rat. Table 3 illustrates the statistical results of the Two-way ANOVAs for each panel showing no effects of estrous cycle. No interactions of estrous cycle and treatment were observed. Numbers at the bottom of bars in panel A represent the number of animals per group, per stage of estrous cycle.

DETAILED DESCRIPTION

Figure 1:
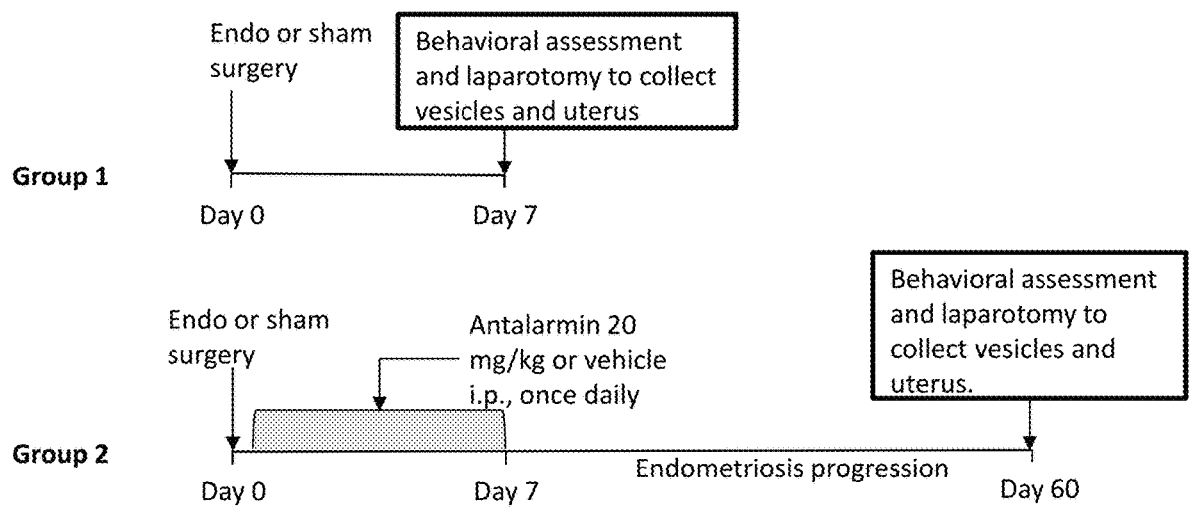
FIG. 1 shows a diagram of experimental protocols; Rats in Group 1 received endometriosis or sham surgery and were allowed to progress for 7 days; Rats in Group 2 received sham surgery or induced endometriosis; Rats from the endometriosis group were injected with either vehicle or antalarmin for seven consecutive days after surgery and allowed to progress for 53 additional days; During the endometriosis progression period, animals were undisturbed except for weekly weighing done at the same time of cage changing.

Presented herein is evidence that a short treatment with the CRHR1 antagonist antalarmin had long-term efficacy in reducing endometriosis with minimal changes in behavior. More importantly, the vesicles that developed were significantly smaller, suggesting that antalarmin interfered with both the establishment and the development of vesicles. It was also demonstrated that antalarmin prevented the increase in CRH and CRHR1 mRNA within endometriosis vesicles as compared to vehicle treated rats, an effect that lasted for almost 2 months after treatment stopped. This suggests that a short treatment will produce long-lasting effects for the treatment of this disease. These results appear to be the first in vivo evidence of efficacy and use of the CRHR1 antagonist antalarmin for the treatment of endometriosis, and open the possibility of further exploring CRH signaling as a treatment target.

In the present disclosure, one-time point was tested corresponding to a major increase in CRHR1 mRNA, early in endometriosis development, as demonstrated herein. Sampson's Theory postulates that retrograde menstruation leads to endometriosis. Based on this theory, during every menstruation, there is opportunity for new endometriosis implants to develop. Therefore, it is suggested that in the clinical scenario, treatment with CRHR1 antagonists would need to be used right after laparoscopic surgery or for several years, similar to contraceptive pills, in order to be effective. In the rat animal model, it was observed that about 60% of the implants sites developed into endometriosis vesicles. A longer or continuous treatment with the CRHR1 antagonist could produce a larger decrease in endometriosis vesicle development or even completely abolish it. In the clinical setting, there is a significant lag in the diagnosis of endometriosis, which is on average 7 years after symptoms appear. This work opens the possibility for future effects of antalarmin or other CRHR1 antagonist at later time points in disease progression.

Not all CRHR1 antagonists are equal. The clinical use of CRHR1 antagonists has been limited by several factors that include lack of consistent efficacy, elevated tissue accumulation and prolonged half-life. Recently, a group of orally administered CRHR1 antagonists have been shown to have high bioavailability and low lipophilicity in animal models of IBS. The availability of these new antagonists opens significant possibilities for the advancement of testing new CRHR1 compounds in endometriosis. However, certain challenges still remain. Eleven isoforms of the CRHR1 receptor have been identified in humans, and splicing of CRHR1 seems to be tissue specific. For example, CRHR1β is present in pituitary myometrium and endometrium, but not in adrenal, placenta, or synovium. It still needs to be determined whether ectopic endometrium will display a different profile of CRHR1 splice variants as compared to eutopic endometrium, both in pre-clinical studies as well as in the clinical setting.

Significant changes in CRH receptors mRNA were observed in the hippocampus of animals treated with antalarmin. While there was significant variability, the data suggest that the increase in receptor mRNA arose as a rebound of the CRHR1 blockade during the first 7 days after endometriosis induction. However, long-term changes in behavior due to the antalarmin administration were minimal. This suggests that compensatory activity most likely occurred in the amygdala and/or other regions involved in controlling anxiety-like behaviors. A recent study using intracerebroventricular administration of antalarmin showed that blocking CRHR1 provides neuroprotection and blunts neuroinflammation resulting from global cerebral ischemia. Blocking CRHR1 in the hippocampus results in a reduction of excitatory activity onto CA3 pyramidal cells in hippocampus. Clinically, CRHR1 signaling has been implicated in mediating abnormal brain responses to expected abdominal pain in patients with IBS. Based on the significant role of CRHR1 in homeostasis and behaviors, one of the challenges is to optimize a CRHR1 peripheral blockade, while producing minimal changes in the brain. This provides an opportunity for drug design that targets peripheral blockade of CRHR1, but prevents lasting effects in brain and behavior.

One of the challenges in the clinical setting is to decrease endometriosis sites, while still preserving reproductive abilities. Antalarmin has been shown in rodents to reduce the number of implantation sites by 70% by a Fas-ligand immune tolerance dependent mechanism. It is possible that antalarmin treatment will compromise reproductive abilities. However, the long-lasting effect of antalarmin in the current results opens the possibility of developing short-term treatments that will provide long-lasting protection and allow for reproductive abilities to return to normal.

A single week of antalarmin treatment was effective in reducing endometriosis in the rat model by 30%. This finding opens the possibility for a new line of treatment for endometriosis by using pharmacological agents that are advanced in the pipeline of clinical trials in safety and efficacy profiles for other inflammatory disorders such as IBS. Translation of this work into the clinic can produce significant benefits for many women that suffer from endometriosis.

Materials and Methods
Animals and Experimental Groups

Female Sprague Dawley rats of 60 days old were used in the experiments (weighing between 190-220 grams). Rats were purchased from Ponce Research Institute Animal Facilities and littermates were never assigned to the same experimental group. Rats were housed two per cage and kept in a 12-hour light/dark cycle with food and water ad libitum. All experimental procedures were approved by the Ponce Health Sciences University (protocol #202) and the University of Texas at Rio Grande Valley (protocol #2016-004) Institutional Animal Care and Use Committees and adhere to the NIH Guide for the Care and Use of Laboratory Animals. Rats were weighed twice per week to monitor their adequate development and once a day during the drug administration period; also, estrous cycles were monitored before and after treatment to assess possible effects of the drug on reproductive cyclicity.

Experiment 1 consisted of 32 female rats that underwent endometriosis induction (n=16) or sham surgery (n=16) and were sacrificed 7 days after surgery (surgery—Day 0; FIG. 1). The main purpose of Experiment 1 was to quantify the levels of CRHR1 mRNA and protein expression at 7 days after endometriosis implantation surgery and thus assess the feasibility of using a CRHR1 antagonist during this period. In addition, anxiety like behavior data were collected (open field and elevated zero maze) as well as plasma levels of corticosterone and ACTH in 8 animals from the sham group and 8 from the endometriosis group.

Figure 14A:
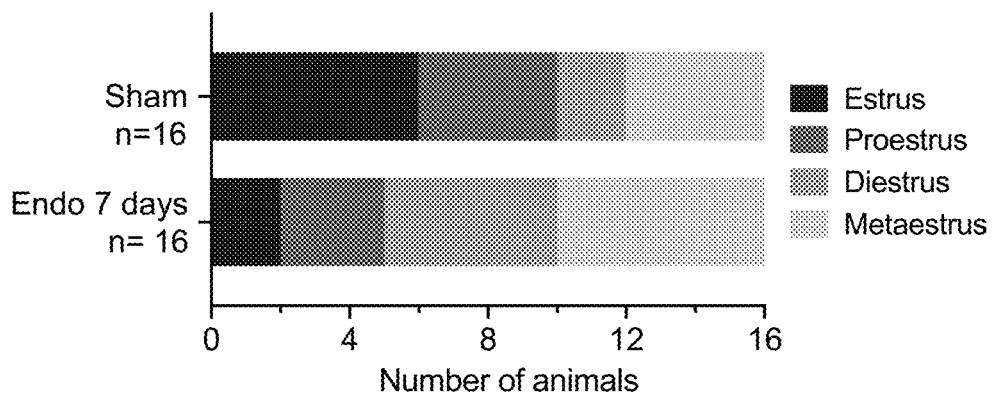
FIG. 14A-14C: Estrous cycle distribution for experiment 1 and experiment 2.
Figure 14B:
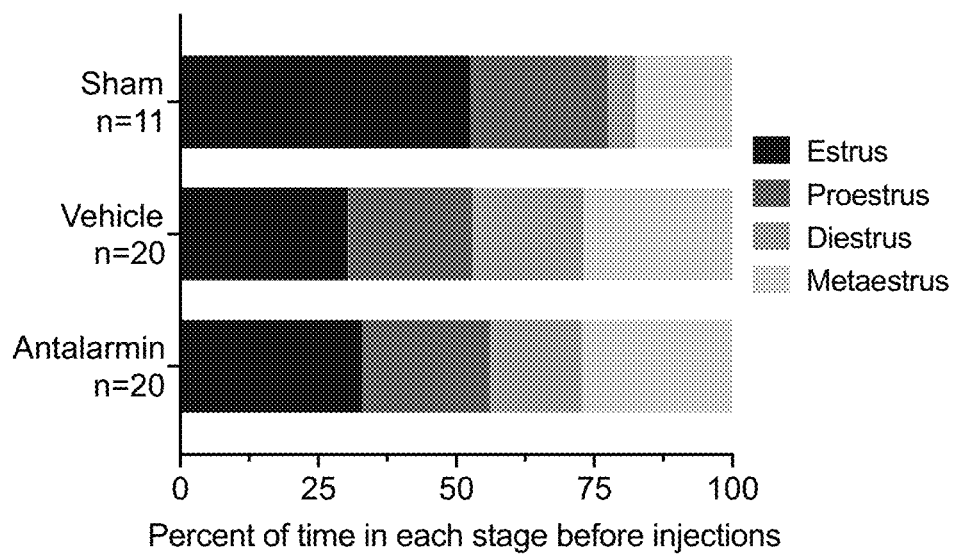
Figure 14C:
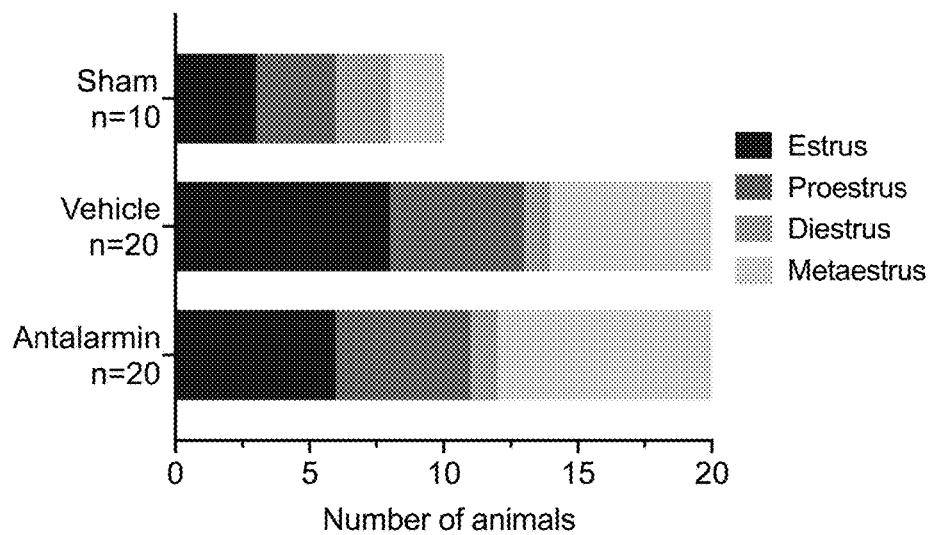
Figure 15A:
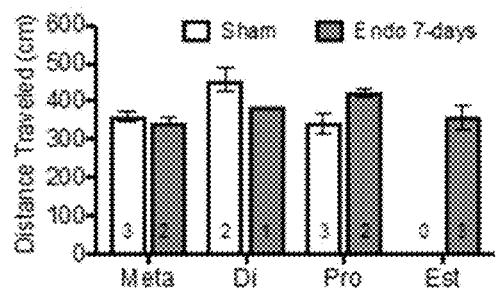
FIG. 15A-15D: Anxiety behaviors at 7 days after endometriosis induction surgery for experiment 1. Estrous cycle stage at the time of sacrifice was measured by vaginal smear. There was no preplan to sacrifice at any particular stage of the cycle but rather at exactly 7 days after the endometriosis induction.
Figure 15B:
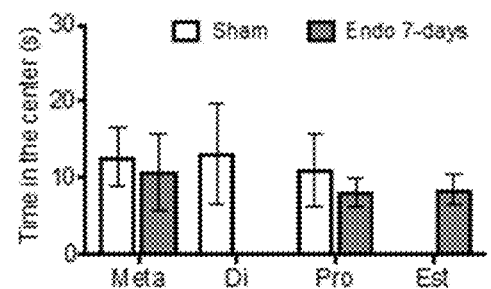
Figure 15C:
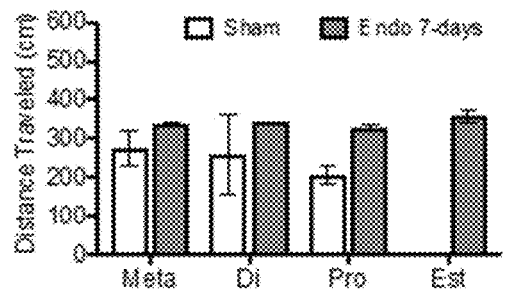
Figure 15D:
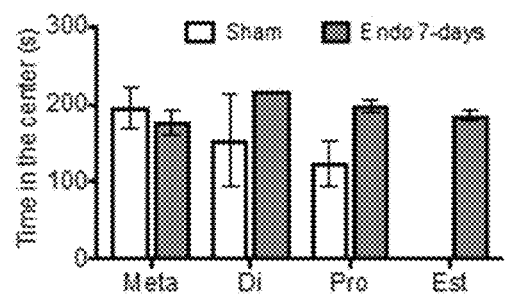
Figure 16A:
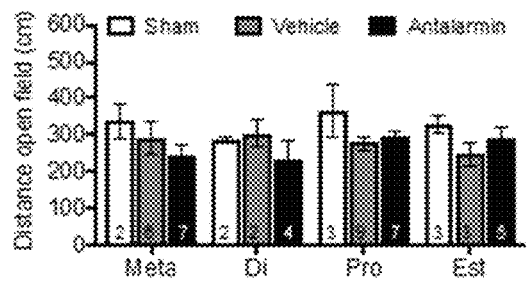
FIG. 16A-16D: Anxiety behaviors at 60 days after endometriosis induction or sham surgery for experiment 2. Similar to experiment 1, estrous cycle stage at the time of sacrifice was measured by vaginal smear. There was no preplan to sacrifice at any particular stage of the cycle but rather at 60 days after the endometriosis induction.
Figure 16B:
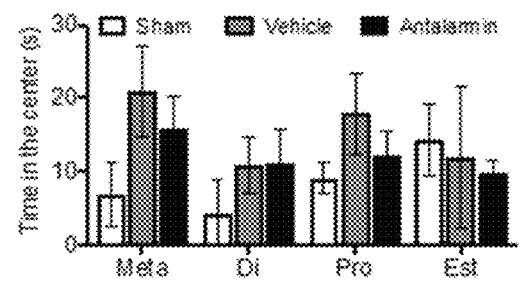
Figure 16C:
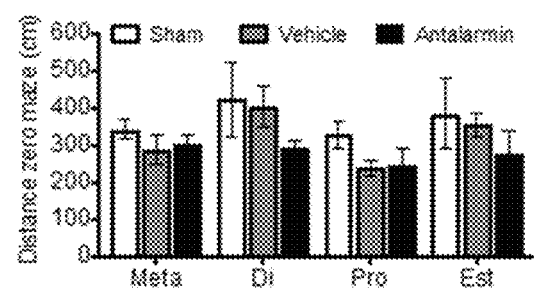
Figure 16D:
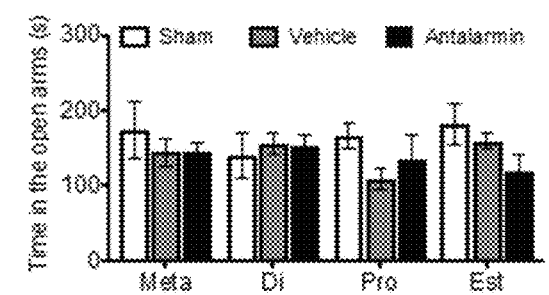
Figure 17A:
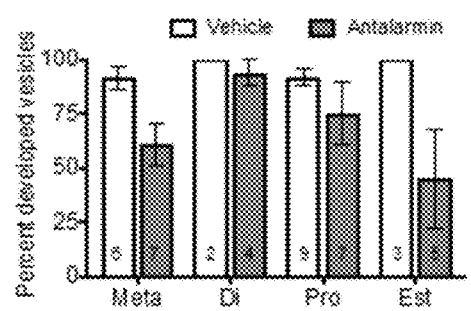
FIG. 17A-17D: Morphological characteristics of endometriosis vesicles illustrated by the stage of estrous cycle at sacrifice.
Figure 17B:
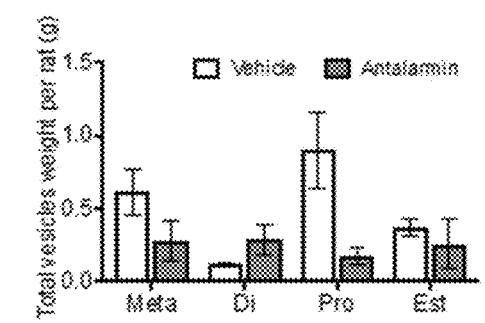
Figure 17C:
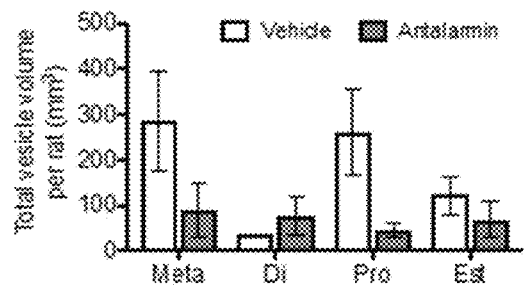
Figure 17D:
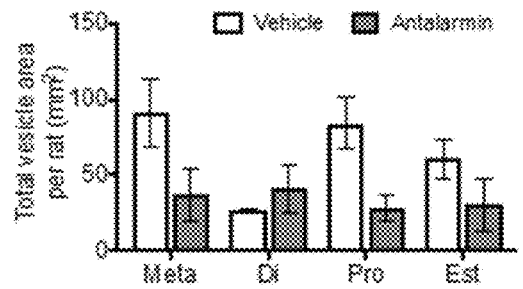
Figure 18:
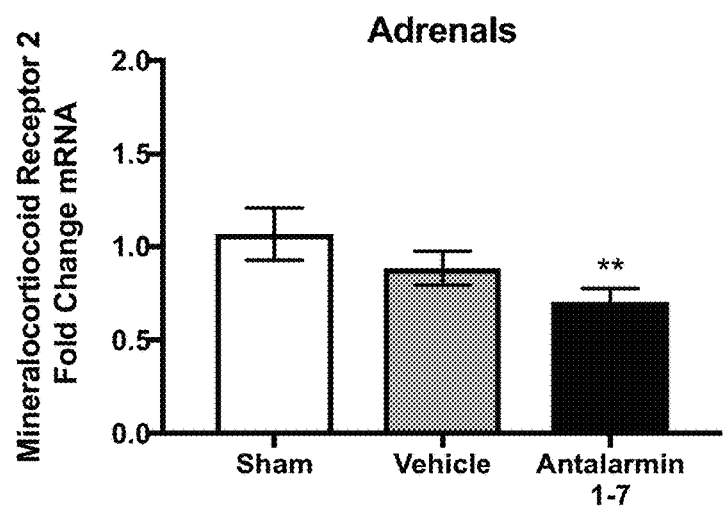
FIG. 18: mRNA of mineralocorticoid receptor 2. Within the adrenal glands of the same animals from the sham or endometriosis groups that received vehicle or antalarmin, the mRNA of the mineralocorticoid receptor 2 was measured. This receptor is in charge of binding adrenocorticotropic hormone (ACTH), which was elevated in animals that received antalarmin. The mineralocorticoid receptor mRNA expression is decreased in response to antalarmin as compared to the sham group. This could be due to a down regulation of the receptor in response to increased ACTH circulating levels. ** $p<0.01$.

Experiment 2 consisted of 51 female rats that underwent endometriosis induction (n=40) or sham surgery (n=11). From the 40 rats that underwent endometriosis induction, 20 rats received the CRHR1 antagonist antalarmin intraperitoneally (i.p.) and 20 rats received vehicle control i.p. (10% Tween 80) from days 1-7 after surgery and endometriosis was allowed to progress until day 60 after surgery. The remaining 11 rats that underwent sham surgery were left untreated until day 60 after surgery. The sham group was used as a non-endometriosis baseline comparison. Only rats with regular estrous cycles were used in the experiments as assessed by vaginal smear lavage during the 7 days prior to surgery and on the day of sacrifice. All but one female from the sham group showed regular estrous cycles before the surgical induction of endometriosis. Therefore, the final group numbers for endometriosis quantification and behavior were: endometriosis-antalarmin=20, endometriosis-vehicle=20, sham=10. Cyclicity was not assessed during the drug administration and was only collected before treatment and the day of sacrifice. This was decided to avoid any additional stressors not related to the drug administration per se that may affect results. The estrous cycle distribution for experiments 1 and 2 can be accessed in FIG. 14.

Various embodiments of the invention are described herein as follows. One embodiment described herein is a method for treating a patient suffering from endometriosis, by administering an effective amount of a CRHR1 antagonist. In another embodiment the patient diagnosed with endometriosis is provided an effective amount of antalarmin.

A method of controlling the symptoms of endometriosis is provided. Symptoms of endometriosis include pain, infertility, inflammation, depression, anxiety, or other stress. The method comprises administering to a patient in need thereof, a therapeutically effective amount of a CRHR1 antagonist. In one embodiment, the CRHR1 antagonist is antalarmin.

Further, the above listed CRHR1 antagonists may be provided as pharmaceutically acceptable salts of an acid or pharmaceutically acceptable bases commonly employed.

In addition to pharmaceutically acceptable salts, other salts are suitable for the disclosed methods and compositions. Also, they may serve as intermediates in the purification of compounds, or in the preparation of other pharmaceutically-acceptable salts, or are useful for identification, characterization or purification.

In one embodiment, a CHRH1 antagonist is provided in combination with a second CHRH1 antagonist. In another embodiment, a CHRH1 antagonist is provided with a CHRH2 antagonist. In another embodiment, a CHRH1 antagonist is provided in a composition, wherein the composition further comprises at least one excipient, a compound that provides better bioavailability, at least one coating, or a combination thereof.

In various embodiments, an agent is optionally applied to the CHRH1 antagonist composition. In one aspect, the agent is selected from the group consisting of a surfactant, a stabilizer, a biomarker for targeting, or a second active pharmaceutical ingredient (API). The term "surfactant," as used herein, is to be interpreted broadly to relate to any composition that is capable of altering "surface tension between a liquid and any precipitated particles suspended in the liquid. Suitable surfactants are taught in McCutcheon's Emulsifiers & Detergents, at pages 287-310 of the North American Edition (1994), and in McCutcheon's Emulsifiers & Detergents, at pages 257-278 and 280 of the International Edition (1994), both published by MC Publishing Co. (McCutcheon Division) of Glen Rock, N.J.

In various embodiments, the CHRH1 antagonist composition is adapted for use as a parenteral formulation. The term "parenteral formulation" refers to a formulation suitable for the administration of the composition via injection under or through one or more layers of skin or mucus membranes of an animal, such as a human. Standard parenteral injections are given into the intradermal, subcutaneous, or intramuscular region of an animal. In some embodiments, a deep location is targeted for injection of a stable nanoparticle compositions. In one embodiment, the parenteral formulation is a subcutaneous parenteral formulation. In another embodiment, the parenteral formulation is an intramuscular parenteral formulation.

In another aspect of the present disclosure, a method of controlling pain resulting from endometriosis in a mammal is provided. The method comprises administering to the mammal in need thereof a therapeutically effective amount of a CHRH1 antagonist composition comprising at least one CHRH1 antagonist. The previously described embodiments of the CHRH1 antagonist composition are applicable to the method of controlling pain resulting from endometriosis in a mammal described herein.

As used herein, the terms "control of pain" or "controlling pain" refer to preventing, minimizing, or eliminating pain in a mammal. As used herein, the term "pain" represents all inflammatory pain and pain associated with endometriosis. The term "pain" also includes pain of varying severity, i.e. mild, moderate and severe pain, as well as acute and chronic pain.

In another embodiment, the pain is acute pain. The term "acute pain" refers to pain resulting from an acute event and generally decreasing in intensity over a period of a few days to a few weeks. In yet another embodiment, the pain is chronic pain. The term "chronic pain" refers to pain resulting from an acute or repeated events and generally increasing in intensity over a period of a few weeks to years.

As used herein, "patient," "subject," or "individual" can be used interchangeably to refer to an animal (mammal). In one embodiment, the mammal is a human.

In carrying out the methods of this disclosure, the amount of CHRH1 antagonist in the CHRH1 antagonist composition is adequate to achieve a therapeutic effect. As used herein, the term "therapeutically effective amount" refers to an amount which gives the desired benefit to an animal and includes both treatment and prophylactic administration. The amount will vary from one mammal to another and will depend upon a number of factors, including the overall physical condition of a mammal and the stage of progression of endometriosis or the level of inflammation correlated to the endometriosis diagnosis.

The amount of CHRH1 antagonist used for the controlling pain gives an acceptable rate of change and maintains desired response at a beneficial level. A therapeutically effective amount of the composition used in the methods of the present disclosure may be readily ascertained by one of ordinary skill in the art using publicly available materials and procedures. In one embodiment of the present invention, the therapeutically effective amount of CHRH1 antagonist to be delivered can be quantified by determining milligrams of CHRH1 antagonist per kilogram of mammal body weight.

In various aspects of the method, the therapeutically effective amount is an amount sufficient to achieve a minimum effective plasma concentration (MEC). Generally, MEC has been defined as the minimum plasma concentration of an analgesic that is sufficient to prevent a patient from requesting a supplementary analgesic. The MEC of a CHRH1 antagonist is well known to the skilled artisan.

In some embodiments of the method, the therapeutically effective amount of a CHRH1 antagonist composition is administered to the mammal at a dose of about 350 mg once per day. This is equivalent to 5 mg/kg in a 70 kg human. In one embodiment, the therapeutically effective amount of the CHRH1 antagonist composition is administered to the animal at a dose of about 0.001 to about 100 mg of CHRH1 antagonist per kg of animal body weight. In another embodiment, the therapeutically effective amount of CHRH1 antagonist composition is administered to the animal at a dose of about 0.01 to about 100 mg of CHRH1 antagonist per kg of animal body weight. In yet another embodiment, the therapeutically effective amount of CHRH1 antagonist composition is administered to the animal at a dose of about 0.1 to about 100 mg of CHRH1 antagonist per kg of animal body weight. In one embodiment, the therapeutically effective amount of CHRH1 antagonist composition is administered to the animal at a dose of about 0.1 to about 10 mg of CHRH1 antagonist per kg of animal body weight. In another embodiment, the therapeutically effective amount of CHRH1 antagonist composition is administered to the animal at a dose of about 1 to about 5 mg of CHRH1 antagonist per kg of animal body weight.

In one embodiment, the therapeutically effective amount of CHRH1 antagonist composition is administered to the animal at a dose of about 1 mg of CHRH1 antagonist per kg of animal body weight. In another embodiment, the therapeutically effective amount of CHRH1 antagonist composition is administered to the animal at a dose of about 2 mg of CHRH1 antagonist per kg of animal body weight. In yet another embodiment, the therapeutically effective amount of CHRH1 antagonist composition is administered to the animal at a dose of about 3 mg of CHRH1 antagonist per kg of animal body weight. In another embodiment, the therapeutically effective amount of CHRH1 antagonist composition is administered to the animal at a dose of about 4 mg of CHRH1 antagonist per kg of animal body weight. In yet another embodiment, the therapeutically effective amount of CHRH1 antagonist composition is administered to the animal at a dose of about 5 mg of CHRH1 antagonist per kg of animal body weight.

In various aspects of the method, CHRH1 antagonist composition is administered as a single dose. In other aspects of the method, the CHRH1 antagonist composition is administered as a single unit dose. As used herein, the term "unit dose" is a discrete amount of the composition comprising a predetermined amount of CHRH1 antagonist. The amount of CHRH1 antagonist is generally equal to the dosage of CHRH1 antagonist which would be administered to an animal or a convenient fraction of such a dosage such as, for example, one-half or one-third of such a dosage.

According to the methods of the present disclosure, the terms "single dose" and "single unit dose" include embodiments wherein the composition can be administered as a single parenteral injection or administered as multiple parenteral injections. In one embodiment, a single dose or single unit dose of the composition can be parenterally administered to an animal at one location on the animal's body. In another embodiment, a single dose or single unit dose of the composition can be parenterally administered to an animal in multiple injections at a single location on the animal's body. In yet another embodiment, a single dose or single unit dose of the composition can be parenterally administered to an animal in multiple injections at more than one location on the animal's body. In embodiments wherein multiple injections of the composition are utilized, the multiple injections can be administered to the animal over a reasonable duration of time.

In another aspect of the present disclosure, a method of treating depression, anxiety or stress caused by endometriosis in a human is provided. The method comprises administering to the animal in need thereof a therapeutically effective amount of a CHRH1 antagonist composition comprising CHRH1 antagonist. The previously described embodiments of the CHRH1 antagonist composition are applicable to the method of treating depression, anxiety or stress caused by endometriosis in a human described herein. The previously described embodiments of the method of controlling pain in an animal, with respect to animals, the amount of CHRH1 antagonist composition is adequate to achieve a therapeutic effect, the therapeutically effective amount of CHRH1 antagonist composition administered to the animal, single doses, and single unit doses are also applicable to the method of treating depression, anxiety or stress caused by endometriosis in a human.

As used herein, the terms "depression", "anxiety", and "stress" are mental disorders that are in connection with the diagnosis of endometriosis. The Diagnostic and Statistical Manual of Mental Disorders, Fourth Edition (DSM-V) has categorized depression based on several symptoms including depressed mood or irritable, decreased interest of pleasure, significant weight change (5%) or change in appetite, change in sleep, change in activity, fatigue or loss of energy, guilt or worthlessness, diminished ability to concentrate, and suicidality. Anxiety is characterized by symptoms including persistent, excessive, and/or unrealistic worry associated with other signs and symptoms, which commonly include muscle tension, impaired concentration, autonomic arousal, feeling "on edge" or restless, and insomnia. Stress disorders are characterized as anxiety after a traumatic event. Stress may also be used colloquially to describe someone as feeling burdened, having the blues, or unhappy.

In various aspects, the pharmaceutical formulation is administered at specified time intervals. In one embodiment, the pharmaceutical formulation is administered once every at least one week. In another embodiment, the pharmaceutical formulation is administered once every at least two weeks. In yet another embodiment, the pharmaceutical formulation is administered once every at least three weeks. In one embodiment, the pharmaceutical formulation is administered once every at least four weeks. In another embodiment, the pharmaceutical formulation is administered once every at least six weeks. In yet another embodiment, the pharmaceutical formulation is administered once every at least two months. In another embodiment, the pharmaceutical formulation is administered once every at least three months.

In one embodiment, a CRHR1 antagonist is administered to a patient in an effective amount to reduce the progression of the disease endometriosis. In another embodiment, a patient diagnosed with endometriosis is administered a single dose of a CRHR1 antagonist. In another embodiment, a patient diagnosed with endometriosis is administered a single dose of a CRHR1 antagonist for seven consecutive days. In another embodiment, a patient diagnosed with endometriosis is administered an effective amount of CRHR1 antagonist continuously over the course of the patient's life. Further, the continuous administration may be one or more doses provided daily, weekly, monthly, bimonthly, every three months, every four months, every five months, every six months, every seven months, every eight months, every nine months, every ten months, every eleven months, or yearly.

In other embodiments, the pharmaceutical formulation further comprises an additional active pharmaceutical agent.

EXAMPLES

The accompanying Examples demonstrate the benefits of blocking CRHR1 with an antagonist, for example antalarmin, to treat endometriosis and reduce endometriosis progression in an animal. First, endometriosis in female rats was induced by suturing uterine horn tissue next to the intestinal mesentery and allowed to progress for 7 days. After 7 days, it was determined that there was a significant increase in CRHR1 within endometriotic vesicles as compared to a normal uterus. Endometriosis was induced in a second group of rats, and further the second group of rats received consecutive doses of antalarmin of 20 milligrams per kilogram intraperitoneal (20 mg/kg, i.p.) during the first 7 days after surgery. A separate group of sham surgery rats served as controls.

Endometriosis in the second group of rats was allowed to progress until 60 days after surgery. At time of sacrifice, rats were tested for anxiety behaviors and endometriotic vesicles, uterus and brains were collected. Rats with endometriosis that received antalarmin significantly decreased the size and number of endometriotic vesicles. Antalarmin also prevented the increase in CRH and CRHR1 within endometriotic vesicles, but not of the glucocorticoid receptor. Within the brain, a non-significant increase in both CRHR1 and CRHR2 mRNA was observed, which might be a rebound effect of the earlier blockade by the seven initial days of treatment. Endometriosis increased anxiety in the zero-maze test, but antalarmin did not modify the effect. These Examples provide the first demonstration for the effective use on CRHR1 antagonist for the treatment of endometriosis, with promising effects for long-term therapy of this debilitating disease.

Example 1

Induction of Endometriosis in a Rat Model and Resulting Elevated Levels of CRHR1

Animals and Experimental Groups

Female Sprague Dawley rats of 60 days old were used in the experiments (weighing between 190-220 grams). Rats were housed two per cage and kept in a 12-hour light/dark cycle with food and water ad libitum. All experimental procedures were approved by the Ponce Health Sciences University and the University of Texas at Rio Grande Valley Institutional Animal Care and Use Committees and adhere to the National Institutes of Health Guide for the Care and Use of Laboratory Animals. Rats were weighed twice per week to monitor their adequate development and once a week during drug administration period. Group 1 consisted of 32 female rats that underwent endometriosis induction or sham surgery (described below) and were sacrificed 7 days after surgery (surgery—Day 0; FIG. 1). This experiment was carried out to quantify the levels of CRHR1 receptors at 7 days after surgery and thus assess the feasibility of using a CRHR1 antagonist during this period. Group 2 consisted of 40 female rats that underwent endometriosis induction or sham surgery and received the CRHR1 antagonist antalarmin or vehicle control from days 1-7 after surgery. Parallel to this group, a separate group of 11 rats underwent sham surgery and were left untreated until day 60 after surgery. Only rats with regular estrous cycles were used in the experiments as assessed by vaginal smear lavage during the 7 days prior to surgery and 7 days before sacrifice.

Endometriosis Induction

Endometriosis was surgically induced. Briefly, rats were anesthetized with isoflurane and four pieces of the right uterine horn were auto transplanted to 4 different blood vessels in the intestinal mesentery. The control group was sham operated animals for which the right uterine horn was massaged for 2 minutes and sutures were placed in the intestinal mesenteric area with no uterine implants. For group 1, sham or endometriosis operated rats were allowed to progress for 7 days after surgery before sacrificed. For group 2, endometriosis was allowed to progress for 60 days before sacrificing.

Sample Collection and Processing

It was verified that the animals were deeply anesthetized. Rats were weighed, and a cytological smear taken to verify stage of the estrous cycle. The peritoneal and thoracic cavities were opened, and a blood sample was collected directly from the heart. Following this, peritoneal fluid was collected using a sterile plastic pipette. Examination was directed to the presence of endometriosis vesicles. The implants that developed into vesicles were excised from the mesentery, weighed and measured using a digital caliper. Classification of vesicles was carried out and assigned the following grades: grade 1=disappeared; grade 2=0.01-1.99 mm; grade 3=2-4.49 mm; grade 4=4.5-5.99 mm; grade 5=6.0 mm or larger. In sham animals, empty suture sites were counted and collected. In addition to the endometriosis vesicles, the adrenal glands were collected, all surrounding fatty tissue was removed, and the cleared adrenal glands were weighed. Additionally, tissues from colon and the left uterine horn were collected. All tissues were flash frozen and stored at −80° until further processing.

RNA isolation and cDNA synthesis

Endometriosis vesicles and normal uterine tissue from endometriosis or sham rats, were lysed in an RLT buffer (QIAGEN, Germantown, Md.) using the BULLET BLENDER Tissue Homogenizer (NEXT ADVANCE, Averill Park, N.Y.). The total RNA from the lysates were extracted according to RNEASY Mini Kit manufacturer's protocol (QIAGEN, Germantown, Md.). RNA concentration and purity were measured on a NanoDrop™ 2000 UV spectrophotometer (Thermo Scientific™, Wilmington, USA). Concentration and quality of RNA samples were acquired based on the ratio of absorbance at 260/280 nm in the spectrophotometer. To carry out the synthesis of cDNA from RNA samples a total reaction volume of 20 μl including 0.1 μg of total RNA concentration and synthesis reagents was used. A iScript™ cDNA Synthesis Kit was used according to manufacturer's protocol (BIO-RAD, Hercules, Calif.). Reactions were carried out in T-100™ thermal cycler (BIO-RAD, Hercules, Calif.). RT-PCR running method was as follows: 25° C. for 5 min, 42° C. for 30 min, 85° C. for 5 min. Samples were stored at −80° C. for later experimentation or qRT-PCR.

Quantitative Real Time PCR Protocol

Real time quantitative PCR (qPCR) was used to evaluate changes in mRNA expression. For this, 25 μl of a total volume of reaction assay was used with 1:10 dilution of cDNA with iQ™ SYBR Green Supermix (BIO-RAD Hercules, Calif.) in a 96 well plate according to the manufacturer protocol and amplified in a Quant Studio™ 12 K Flex Real time PCR System (Applied Biosystems™, Carlsbad, Calif.). Commercial primers for CRH, UCN1 CRHR1, CRHR2 and glucocorticoid receptor (GR) were purchased from QIAGEN (Germantown, Md.). Real time PCR cycles protocol was as follows: 95° C. for 10 min. for enzyme activation followed by 40 cycles of denaturing at 95° C. for 15 sec. and annealing at 60° C. for 1 min. All changes in gene expression were normalized against GAPDH of each sample. CT values and changes per gene expression level were automatically analyzed by the Quantstudio™ 12 K Flex Software (Applied Biosystems™, Carlsbad, Calif.). All samples were run in duplicate. For comparison purposes, mRNA from sham rats were always run within the same plate as experimental samples from vehicle treated and antalarmin treated groups.

Statistical Analyses

GraphPad Prism 6.0 (GraphPad Software, San Diego, Calif.) was used to prepare graphs and run statistical analyses. Data is presented as mean difference+SEM and a p value <0.05 was considered statistically significant. The variability between groups was first assessed followed by a test for outlier values. A Student t-test was used for comparisons between two groups and when group variability was significantly different, a Welch corrected t-test was used. A One-way analysis of variance (ANOVA) was used to compare behaviors. A one-sample t-test against the sham rats value normalized to 1.0. was used to assess RT-PCR results. A repeated measures One-way ANOVA was used to compare changes in weight gain between treatment groups.

CRHR1 is Elevated in Group 1 Rats with Induced Endometriosis.

Figure 2:
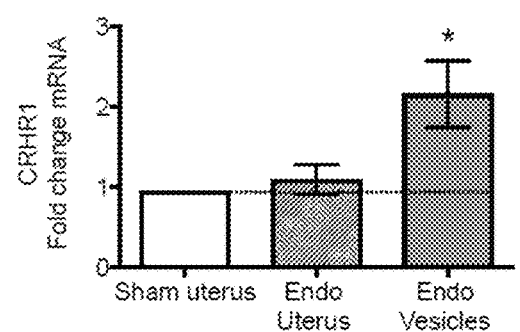
FIG. 2 shows a graph of qRT-PCR of CRHR1 within endometriosis vesicles and uterus of the endometriosis rats and sham rats; At 7 days after the autotransplantation surgery, a significant two-fold increase was observed in CRHR1 mRNA only within endometriosis vesicles.

To evaluate the early endometriotic vesicle development, a first group of rats were induced with the disease and sacrificed after 7 days. It is during this early development period that the major changes in CRHR1 could be observed. At 7 days, 93.7% of the implants had created a large vesicle, which in most cases was very large and filled with fluid. In the sham group, only sutures were observed as no uterus was transplanted. Table 1 shows the morphological characteristics of the observed vesicles at 7 days post-induction surgery. CRHR1 mRNA was quantified in the vesicles as compared to the normal uteri of the same rats and that of sham surgery controls. CRHR1 mRNA in endometriosis vesicles showed a two-fold increase as compared to normal uterus of sham rats (t=2.934, d.f.=6, p<0.05; FIG. 2). In contrast, the mRNA levels in uteri of rats that received endometriosis were not different from the uteri of sham rats (t=0.829, d.f.=6, p>0.05; FIG. 2).

TABLE 1

Characteristics of endometriosis Vesicles at seven days after transplantation surgery

| | Endo vesicles at 7 days | | | |
|---|---|---|---|---|
| | Percent developed (%) | Total weight (g) | Total area (mm²) | Total volume (mm³) |
| Average per rat ± S.E.M. | 93.75 ± 2.80 | 1.19 ± 0.25 | 160.92 ± 15.64 | 2190.25 ± 1110.58 |

Example 2

Antalarmin's Effect on Stress Reactivity or Anxiety Behaviors in Group 2 Rats

Behavioral Assessment

One day before behavioral assessment and sacrifice a subset of rats (6 vehicle and 6 antalarmin) were subjected to an acute episode of swim stress of 10 min and compared to no stress controls to assess how rats respond to acute activation of the HPA axis. For this, animals were placed in a Plexiglas tank for 10 min in water at 25° C. Rats were towel dried and kept in warm cage after swim until fur dried. The next day, two behavioral tasks were used to assess anxiety behaviors. The open field test is used to quantify exploratory and locomotor activity of a rodent in an open arena. The apparatus used was a square wood arena (91× 91×38 cm) with overhead light illumination and video monitoring to record animal activity using Any-Maze software (Stoelting, Wood Dale, Ill.). The following behaviors were quantified during 20 minutes: 1) total distance moved, 2) time spent moving, 3) time spent in the center of the arena, 4) time spent near the walls of the arena (defined by the 15 cm of floor arena closest to the walls) and 5) total fecal pellets. The more time the animal spends in the center of the arena compared to the space adjacent to the wall is considered as having less anxiety. At the end of the testing period, animals were returned to the home cage and after a 5-min break were tested in the elevated zero-maze.

The elevated zero-maze is very similar to the more traditional elevated plus maze test, with the advantage of not having a neutral (undefined) zone in the middle. The apparatus consisted of a circle with an arm width of 10 cm and elevated 40 cm from floor. Two sections of the circle were open without walls and two enclosed by 40 cm high walls. Rats were placed in the intersection of an open arm, facing the closed arm and opposite to the experimenter. Rats were allowed to run the maze for 5 consecutive minutes and recorded using the Any-Maze software (Stoelting, Wood Dale, Ill.). The following parameters were analyzed by the Any-Maze program: 1) total distance travelled in the maze, 2) time spent in the open/closed arms and 2) number of entries made by the rodent onto the open/closed arms. When 60% of the animal body entered the arm, the program counted is as an entry. In addition, total fecal pellets in the maze were quantified. The more time the animal spends in the open arms is considered as having less anxiety. After the 5-min testing period, the rat was returned to the home cage and immediately anesthetized with an overdose of 65% sodium pentobarbital to proceed with laparotomy. The maze was thoroughly cleaned with 70% alcohol solution before testing the next rat.

Antalarmin Did not Affect Stress Reactivity or Anxiety Behaviors

Figure 3A:
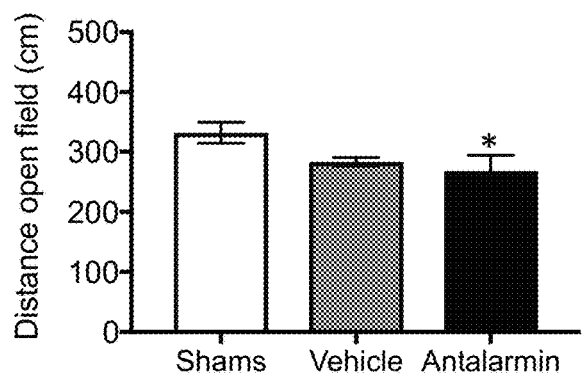
FIGS. 3A-3D exhibit behavioral assessment for anxiety; Rats that received sham surgery, or endometriosis and antalarmin, or vehicle treatment, were tested in the open field (FIG. 3A and FIG. 3B) or in the elevated zero maze (FIG. 3C and FIG. 3D); In comparison to sham, a significant decrease in locomotor activity of the group that received antalarmin was observed; However, time spent in the center of the open field was not different between groups; In the elevated zero maze, a significant increase in locomotion was observed for rats that had endometriosis as compared to sham, regardless of the drug treatment (FIG. 3C). Rats with endometriosis, regardless of drug treatment, showed a trend towards spending less time in the open segment of the zero maze as compared to sham group. * represents $p<0.05$.
Figure 3B:
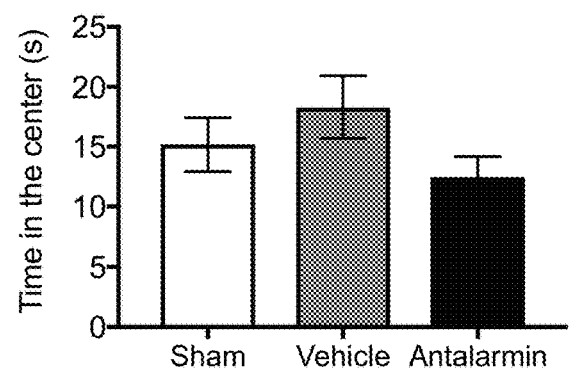
Figure 3C:
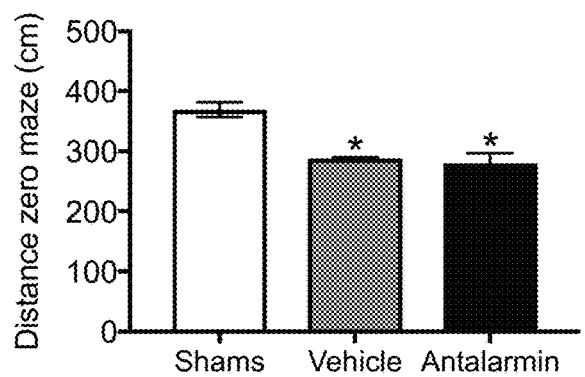
Figure 3D:
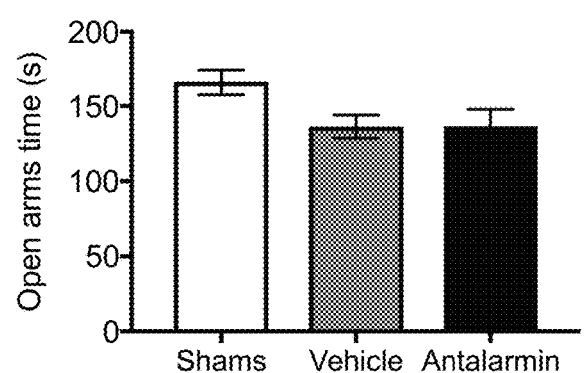

To block the significant increase in CRHR1 receptor within the endometriotic vesicles, antalarmin was administered during the first 7 days after endometriosis induction surgery as described in Example 1. After that, the endometriosis was allowed to progress for 53 additional days. At Day 59, after endometriosis surgery, a subset of the animals (6 vehicle and 6 antalarmin) were subjected to a 5-min swim stress challenge. Antalarmin treated animals (as described in Example 1) were not different from the control group in any of the behavioral parameters measured such as immobility, swimming, struggling behaviors, and diving episodes (data not shown). Therefore, rats tested in the stress challenge were collapsed within the not-tested ones within treatment groups (vehicle or antalarmin as described in Example 1). The next day, all animals were tested using the open field and the zero maze to evaluate trait and state anxiety, respectively. The total distance traveled (FIG. 3A) was significantly lower in rats that received antalarmin as compared to the sham group [(F(2,45)=3.507, p<0.05)], but the amount of time rats spend in the center of the open field arena was similar between groups [(F(2,45)=0.12, p>0.05; FIG. 3B)]. On the zero maze, a higher locomotor activity was observed for both groups of rats with endometriosis that received vehicle or antalarmin compared to the sham group (F(2,49)=6.01, p<0.01; post-hoc, 0.01 both comparisons; FIG. 3C). Despite a higher locomotor activity, there was a strong trend for both groups of rats with endometriosis to spend less time in the open arms of the zero maze [(F(2, 49)=2.82, p=0.06; FIG. 3D)] suggesting increased anxiety. In summary, antalarmin administered shortly after endometriosis induction (as described in Example 1) does not have long-term effects on anxiety behaviors. However, endometriosis increased anxiety in the zero-maze compared to sham controls, regardless of treatment.

Example 3

Antalarmin Reduced the Size and Number of Vesicles Developed in Group 2 Rats

Figure 4A:
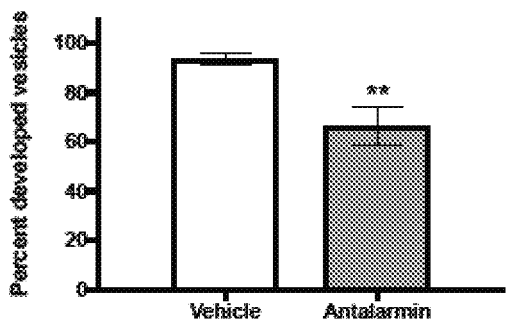
FIGS. 4A-4E show morphological characteristics of endometriosis vesicles.
Figure 4B:
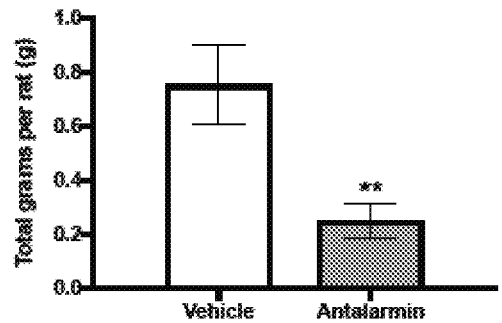
Figure 4C:
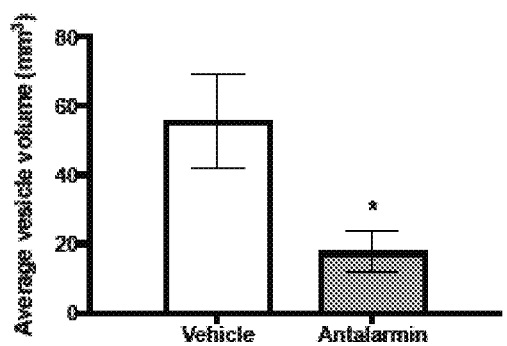
Figure 4D:
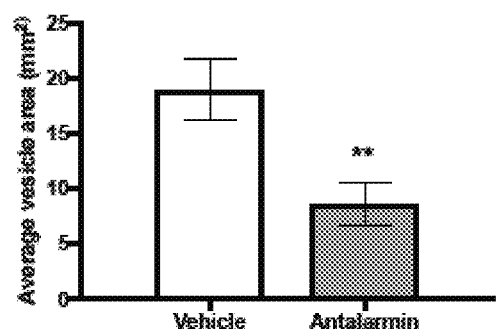
Figure 4E:
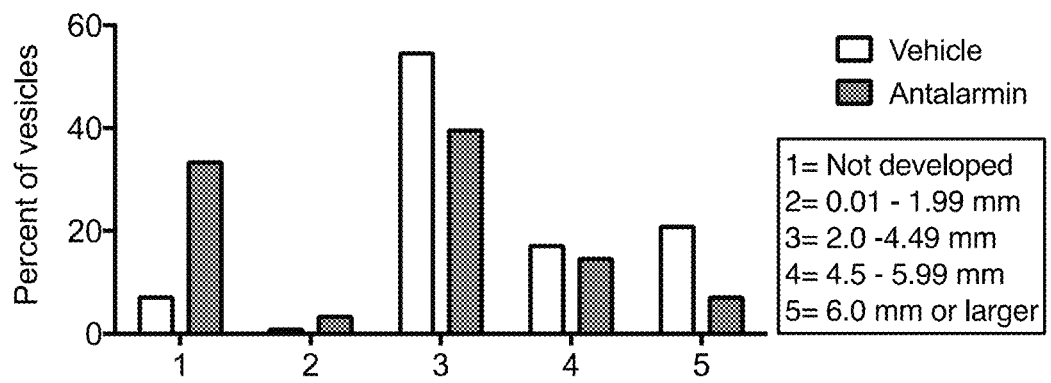

Antagonizing CRHR1 Early in Endometriosis Produced a Significant Decrease in Vesicle Development Rats were maintained as described in Example 1. As described in Example 1, antalarmin was administered during the 7 days after endometriosis induction resulted in a 30% significant decrease in the number of developed endometriosis vesicles at 60 days (Welch corrected t-test, t=3.38, d.f.=22.86, p<0.01; FIG. 4A). After sacrifice, the vesicles were collected according to methods provided in Example 1. The total weight of endometriosis vesicles (sum per rat) in the antalarmin treated group was 67% less than the vehicle control group (t=3.175, d.f.=38, p<0.01; FIG. 4B). The reduced weight was a direct result of the smaller size of the vesicles in average volume (68% difference, Welch corrected, t=2.515, d.f.=25.39, p<0.05; FIG. 4C) and area (55% difference, t=3.067, d.f.=38, p<0.01; FIG. 4D) per rat. As described in Example 1, vesicles were classified in grades (1-5) based on a length scale for each vesicle where 1 denotes an implant that disappeared and 5 an implant that developed into a vesicle equal or larger than 6 mm (FIG. 3E). In the antalarmin treated group compared to the vehicle treated control, there was a larger percentage of endometriosis vesicles that disappeared, as well as a reduced percentage of vesicles of grade 3 and 5. In summary, seven days of antalarmin treatment resulted in a smaller percentage of endometriosis implants developed and those that did develop were significantly smaller in size.

Example 4

Antalarmin's Effect on ACTH Serum Levels

Enzyme Linked Immunosorbent Assays (ELISA)

Serum and peritoneal fluid samples from animals were tested for levels of corticosterone, adrenocorticotropic hormone (ACTH) and the pro-inflammatory cytokine IL-6 following instructions in the commercial kits. The following kits were used: Corticosterone rat/mouse kit (Cat. #79175; IBL America, Minneapolis, Minn.); Rat IL-6 pre-coated ELISA kit (Cat. #437107; BioLegend, San Diego, Calif.); Mouse/rat ACTH ELISA kit (Cat. # AC018T-100, Calbiotech, El Cajon, Calif.).

Antalarmin Produced a Long-Lasting Increase in Serum ACTH

Figure 5A:
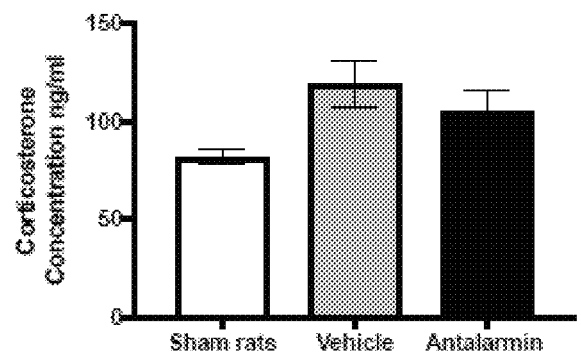
FIGS. 5A-5C show serum and peritoneal markers of stress and inflammation; An ELISA was used to measure (FIG. 5A) corticosterone and (FIG. 5B) adrenocorticotropic hormone (ACTH) in the serum of rats and (FIG. 5C) IL-6 in peritoneal fluid at the time of sacrifice. There was no significant difference between groups in serum corticosterone levels at the time of sacrifice of the rats; However, a significantly higher level of ACTH was observed between vehicle and antalarmin groups; Statistical comparison of ACTH with the sham group was limited due to the small sample size (n) in this particular group. No differences in IL-6 were observed between groups. *represents $p<0.05$.
Figure 5B:
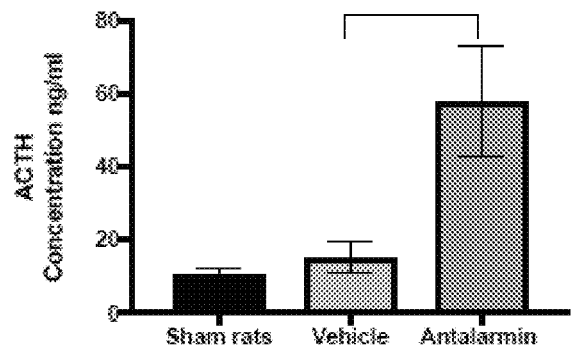
Figure 5C:
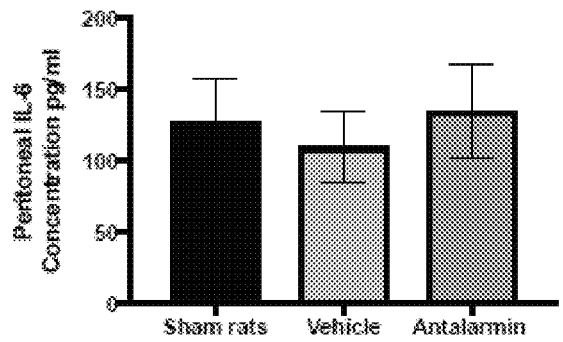

At the time of sacrifice, peritoneal fluid and blood serum was collected from rats according to methods described in Example 1. The samples were examined to understand how the treatment with antalarmin might have altered HPA axis markers and also the pro-inflammatory cytokine IL-6. Corticosterone was slightly elevated in rats with endometriosis treated with vehicle or with antalarmin, however this apparent difference, did not reach statistical significance [(F(2, 43)=1.99, $p>0.05$; FIG. 5A)]. However, significantly elevated levels of serum adrenocorticotropic hormone (ACTH) were observed in rats that received antalarmin compared to the vehicle treated group as described in Example 1. Some samples ran for ACTH returned values that were under the detectable limit of the ELISA kit used. Thus, only 2 rats in the sham group, 11 in the vehicle group and 12 in the antalarmin group were able to be quantified. Despite this experimental difficulty, a t-test between vehicle and antalarmin groups revealed a significant difference between treatments [(t=2.62, d.f.=21, $p<0.05$; FIG. 5B)]. While anti-inflammatory effects of antalarmin have been reported, the short treatment 53 days before sacrifice did not produce any change in IL-6 in peritoneal fluid, which is in direct contact with the endometriotic vesicles (FIG. 5C).

Example 5

Antalarmin Blocked mRNA Increase in CRH and CRHR1 of Uterus and Vesicles.

Figure 6A:
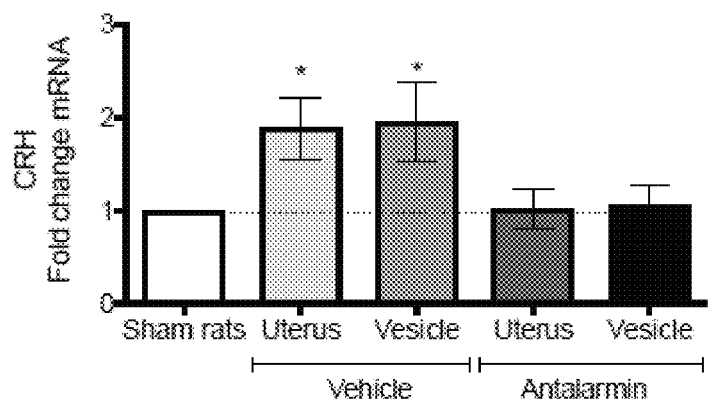
FIGS. 6A-6B show mRNA levels measured by qRT-PCR from the uterus and endometriosis vesicles.
Figure 6B:
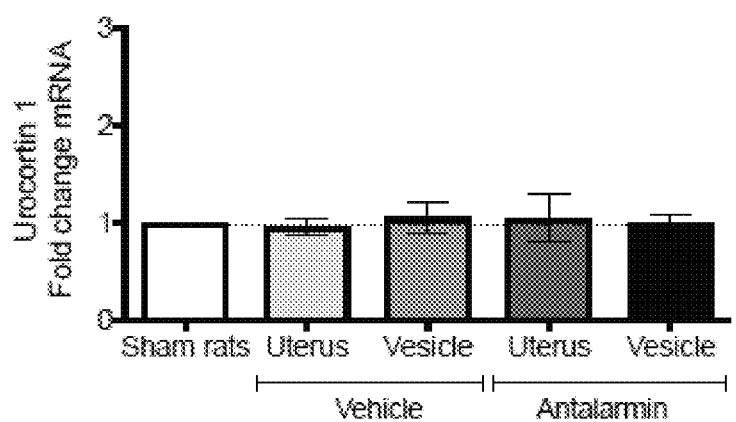

The mRNA for urocortin and CRH was quantified using methods described in Example 1, which are the main agonists of the CRHR1 receptor, within developed endometriosis vesicles in rats from both treatment groups using qRT-PCR. As a comparative parameter, the mRNA with the uteri of the same animals was also quantified and used uteri of sham controls to normalize the data. A significant two-fold increase in CRH for vehicle treated rats, both in uterus (one sample t-test: t=2.66, d.f.=13, $p<0.05$) and vesicles (t=2.29, d.f.=13, $p<0.05$; FIG. 6A) was observed. However, this increase was not observed in the antalarmin treatment group (FIG. 6A). In contrast, UCN1 mRNA was not altered in any of the groups measured (FIG. 6B).

Figure 7A:
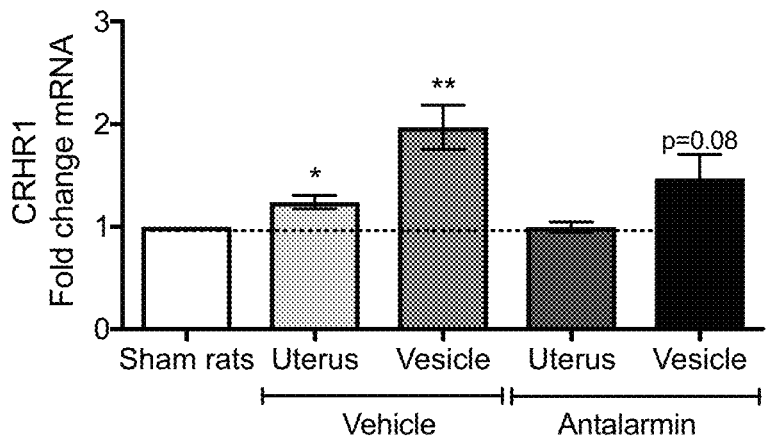
FIGS. 7A-7C show graphical results of mRNA levels of measured by qRT-PCR from the uterus and endometriosis vesicles.
Figure 7B:
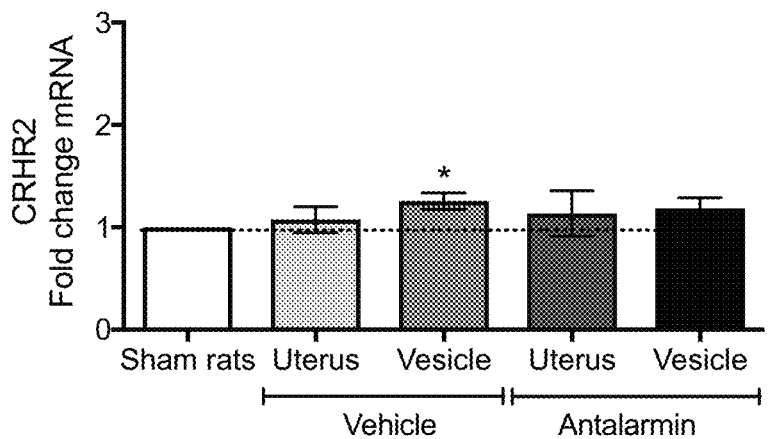
Figure 7C:
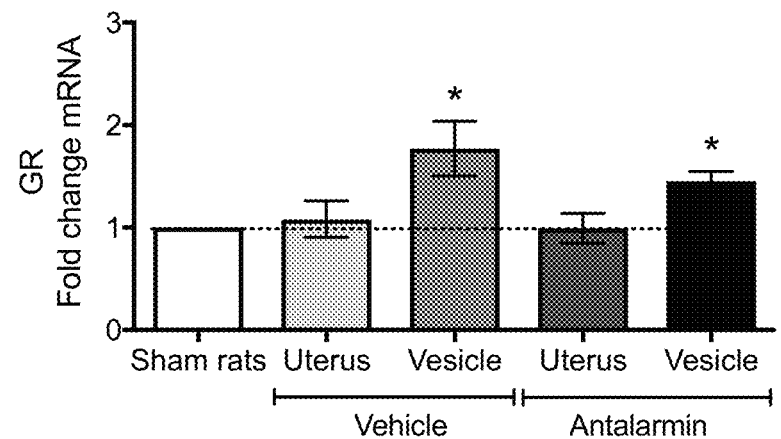

The mRNA quantification and sample collection were done in accordance with the procedure provided in Example 1. The mRNA of the CRHR1 receptor measured in endometriosis vesicles of the vehicle group was significantly increased as compared to sham uterus (t=3.45, d.f.=8, $p<0.01$; FIG. 7A), but this increase was not observed in the vesicle of antalarmin treated rats ($p>0.05$). Due to the intricate balance of CRH receptor activity in uterine tissue the CRHR2 receptor mRNA, was also quantified. For this receptor, a small but significant fold increase in mRNA was observed only in the vesicles of vehicle treated animals (t=3.2, d.f.=8, $p<0.05$; FIG. 7B). No other changes were observed for CRHR2. The glucocorticoid receptor (GR) showed an interesting pattern with a significant mRNA fold increase that was observed in vesicles from both, the vehicle treated (t=2.88, d.f.=8, $p<0.05$; FIG. 7C) and antalarmin treated (t=4.65, d.f.=8, $p<0.01$; FIG. 7C) groups, but no changes in uterus.

Example 6

The Effect of Antalarmin and Endometriosis on the Brain

Figure 10A:
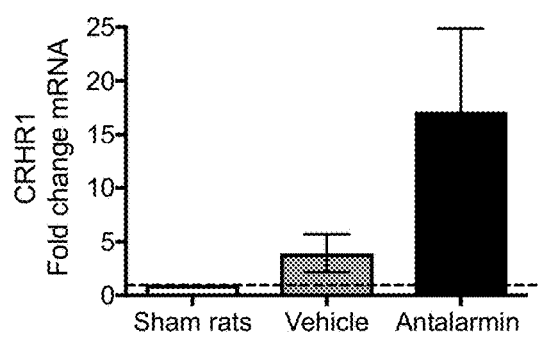
FIG. 10A-10E: mRNA levels measured by qRT-PCR from the hippocampus of sham and endometriosis groups with vehicle or antalarmin treatment.
Figure 10B:
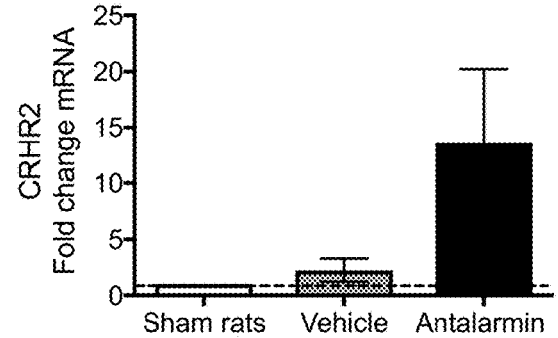
Figure 10C:
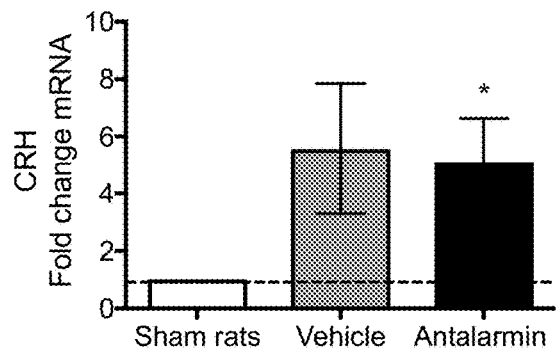
Figure 10D:
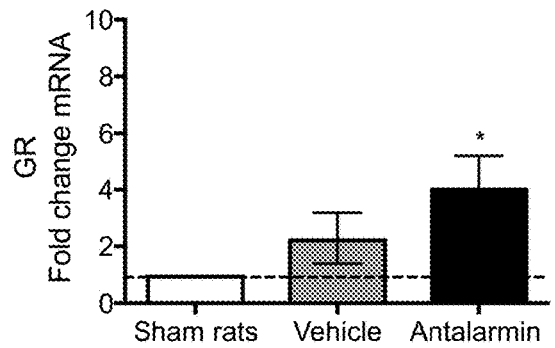
Figure 10E:
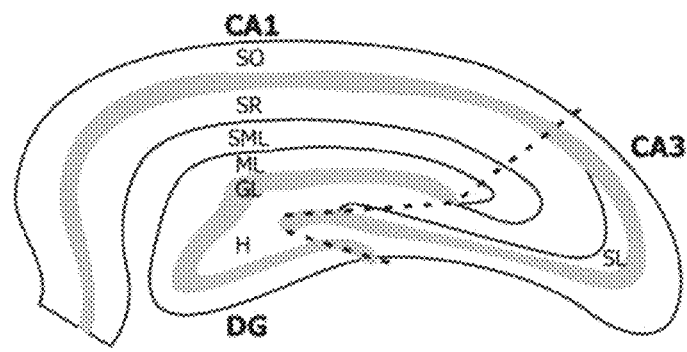
Figure 11A:
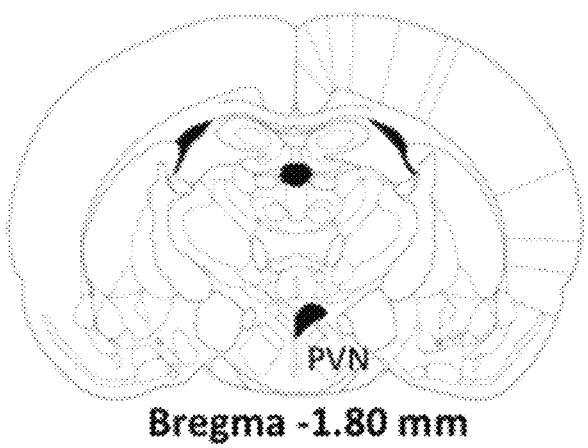
FIG. 11A-11D: Percent of area immunolabeled by CRH peptide in the hypothalamus and hippocampus of sham and endometriosis groups with vehicle or antalarmin treatment.
Figure 11C:
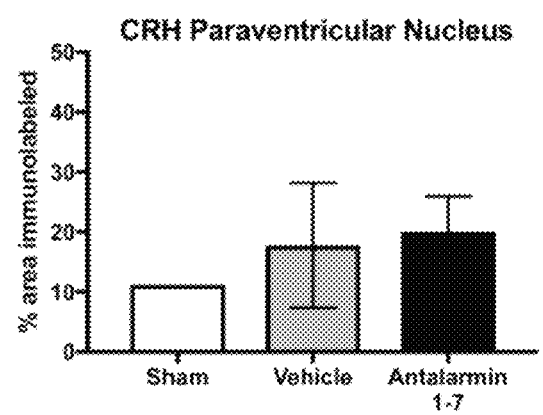
Figure 11D:
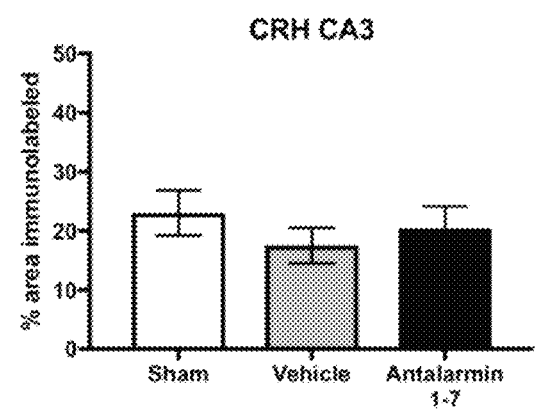
Figure 11B:
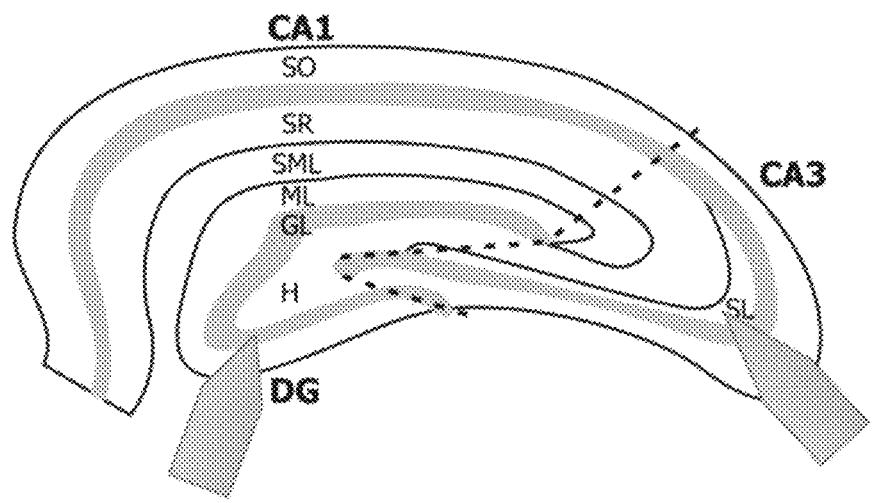
Figure 12A:
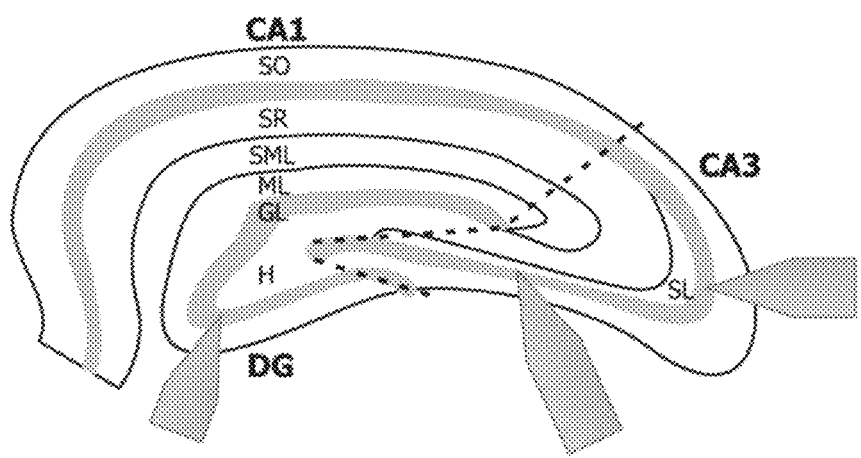
FIG. 12A-12D: Percent of area immunolabeled by CRH receptor type 1 (CRHR1) in the hippocampus of sham and endometriosis groups with vehicle or antalarmin treatment.
Figure 12B:
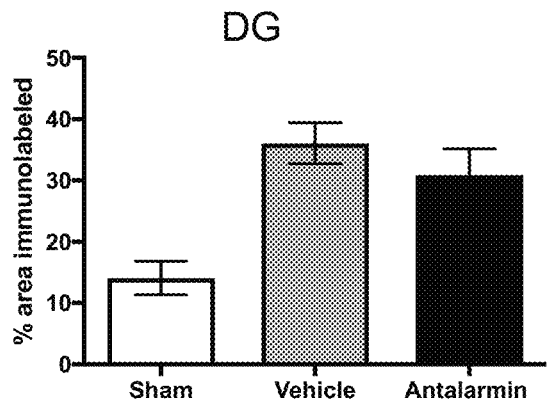
Figure 12C:
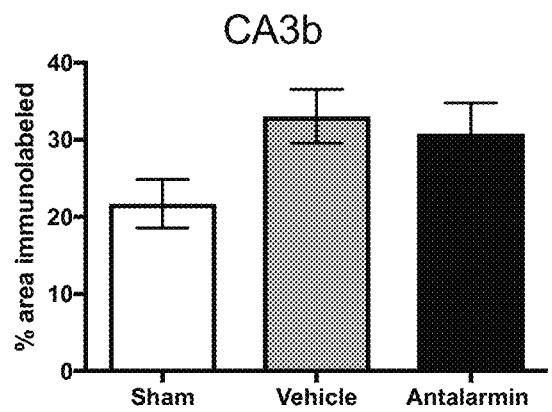
Figure 12D:
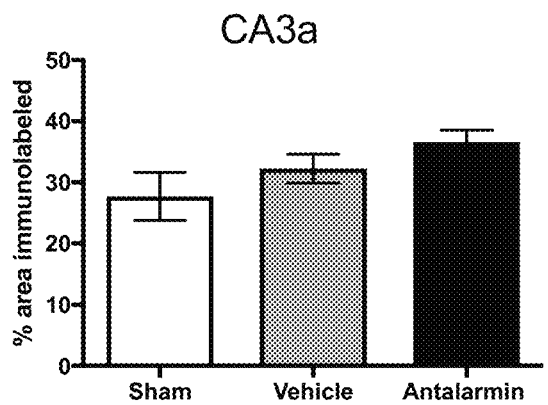
Figure 13A:
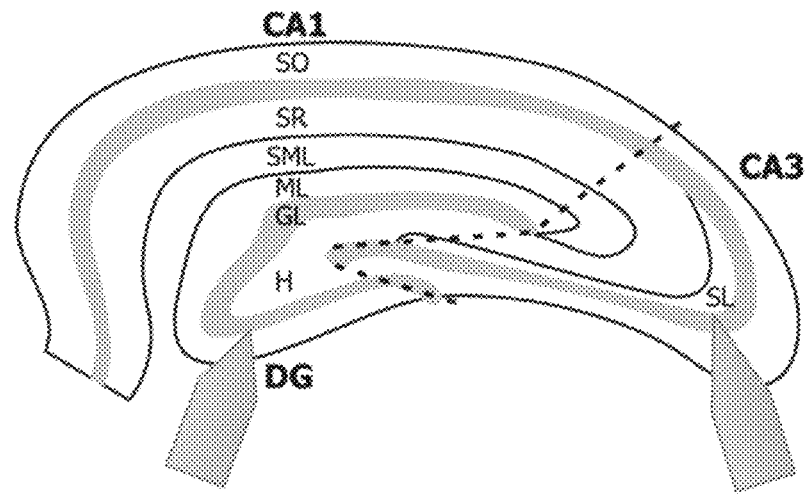
FIG. 13A-13C: Percent of area immunolabeled by glucocorticoid receptor (GR) in the hippocampus of sham and endometriosis groups with vehicle or antalarmin treatment.
Figure 13B:
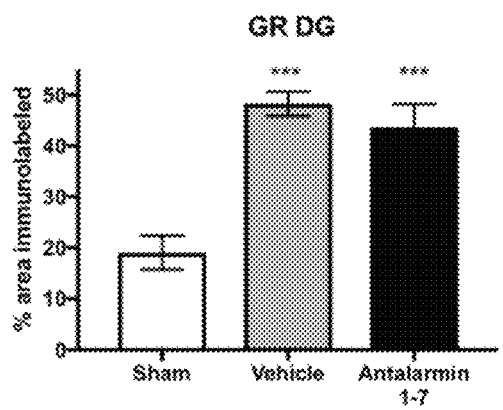
Figure 13C:
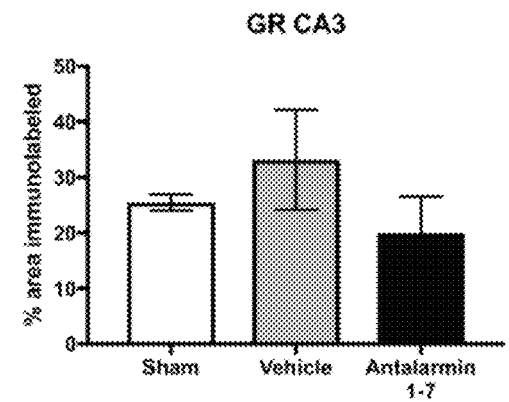

Endometriosis and antalarmin have long-lasting effects in the brain. Previous work reported a decrease in CRH within hippocampus of animals with endometriosis compared to sham rats that were subject to stress. Given that antalarmin readily crosses the blood brain barrier, the effects of treatment in the hippocampus was quantified. CRHR1 and CRHR2 showed a 15-fold increase in rats that received antalarmin, but this increase also showed a large variability within the group. It appears that the increase in CRH1 was balanced out by an equally similar increase in CRH2. This was not observed in the vehicle treated groups (FIGS. 10A and 10B). mRNA was collected and quantified as described in Example 1. Endometriosis caused an increase in hippocampal CRH mRNA of similar magnitude both in vehicle treated and antalarmin treated groups. However, only the antalarmin grouped reached statistical significance as compared to sham (t=2.70, d.f.=6, $p<0.05$). The GR mRNA showed a twofold increase in vehicle treated rats compared to sham (t=1.44, d.f.=6, $p>0.1$) and a fourfold increase in the antalarmin treated group (t=2.71, d.f.=6, $p<0.05$). In summary, antalarmin caused persistent changes in the brain that lasted long after the treatment stopped.

Brain Immunohistochemistry Protocols

Protocols previously published (Torres-Reveron et al., 2016, 2009, 2008) were followed. Rats were perfused with 4% paraformaldehyde by aortic arch perfusion and brains were removed and stored in cryoprotectant solution (30% sucrose, 30% ethylene glycol) until further processing. Coronal tissue sections (40 μm thick) through the hypothalamus (sections 0.92 to 1.88 caudal to Bregma) and dorsal hippocampus (sections 3.8 to 4.3 caudal to Bregma), which include the amygdala were selected and incubated in antiserum raised against CRHR1 (goat polyclonal, Abcam, cat. ab59023), CRH peptide antibody (guinea pig polyclonal, Peninsula labs., cat. T-5007) or glucocorticoid receptor antibody (GR, rabbit monoclonal, Cell Signaling cat. #3660) for 48 hrs. at 4° C. Optimal working concentrations were determined for each antibody. The primary antibody was labeled with CY3 secondary antibody (1:400 Jackson ImmunoResearch, West Grove, Pa.). Images were taken at the same time and illumination (excitation) and background corrected to control for batch effects. All regions of interest were analyzed using Image J software (open access from NIH) to calculate the percent of positive immunolabeling within the region of interest. Tissue from control and experimental animals was processed together. For each animal, the two best morphologically preserved sections of each region of interest were included in the analysis.

Results

Conclusions from analysis of data presented in FIGS. 10-13 are as follows:

The dentate gyrus, which is involved in stress regulation, appears to be particularly sensitive to endometriosis because increases in both GR and CRHR1 receptor were observed in this region.

While antalarmin treatment produced no effects, this could be due in part to the fact that treatment ceased 53 days earlier.

Limbic regions in the brain can reflect changes produced by endometriosis in the peritoneal cavity.

Example 7

Antalarmin decreased body weight and the decrease persisted in treated animals.

Figure 8A:
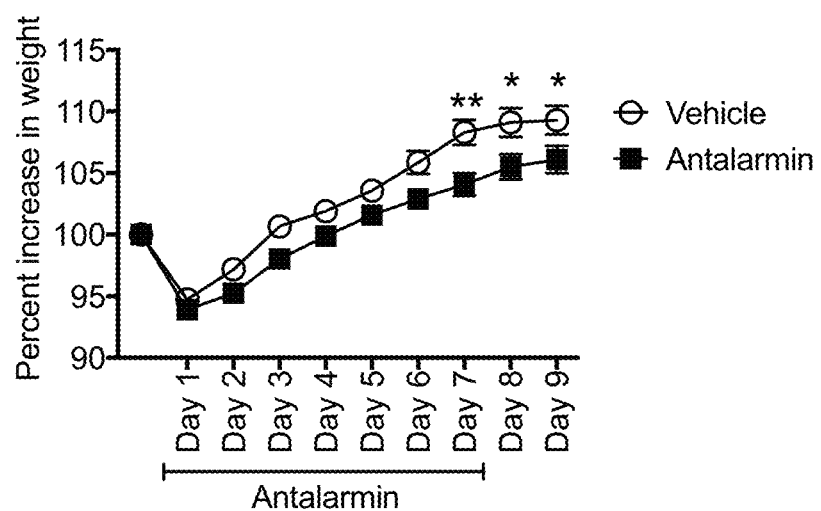
FIGS. 8A-8B show the percent increase in weight for rats with endometriosis treated with antalarmin or vehicle (FIG. 8A) After seven days of treatment, antalarmin treatment significantly decreased the weight of the rats, and this difference persisted for two additional days after the drug treatment had stopped.
Figure 8B:
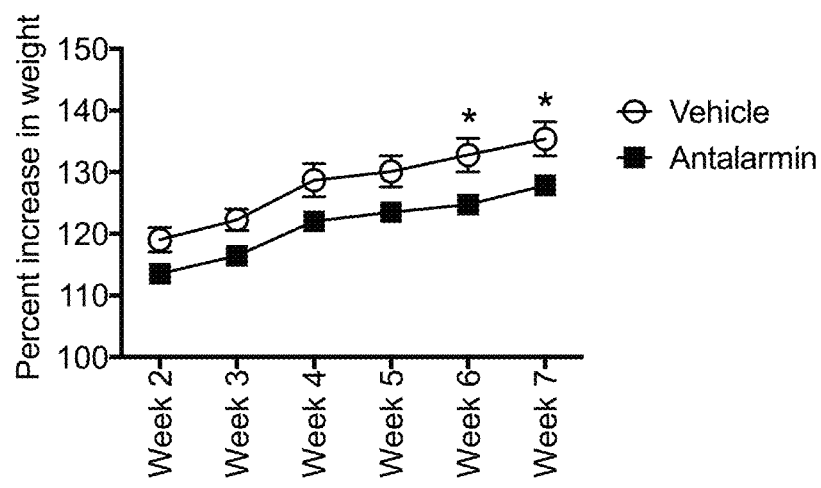
Figure 9:
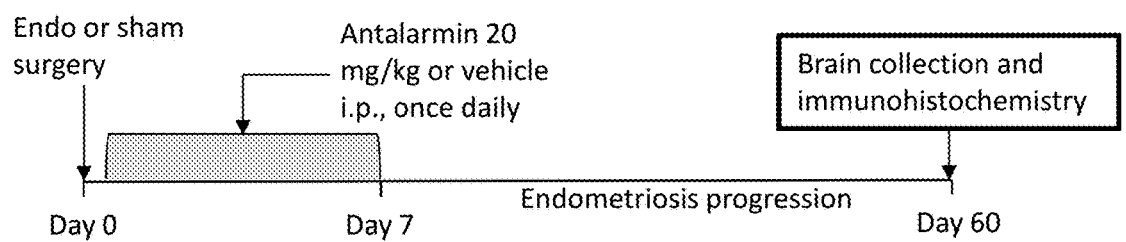
FIG. 9: Experimental timeline studies of hippocampus.

Inconsistencies in the effect of antalarmin on male rodent body weight can happen. The Group 2 rat weight changes were monitored during the drug administration period and every week afterwards during the development of endometriosis. By day 7 and for 2 days after antalarmin had stopped, rats receiving the drug weighed significantly less than vehicle control groups (Repeated measures ANOVA of treatment: $F(1,38)=7.615$, $p<0.01$, post hoc, $p<0.01$ on day 7 and $p<0.05$ on days 8 and 9; FIG. 8A). While the rats maintained a constant weight gain rate, by week 7 and 8 after endometriosis induction (FIG. 8B), a significantly lower weight gain compared to vehicle group was also recorded ($F(1,38)=33.89$, $p<0.001$, post hoc, $p<0.05$ for weeks 6 and 7).

TABLE 2

Two way ANOVA summary of statistics

| Parameter | Effect of treatment | Effect of cycle | Interaction |
|---|---|---|---|
| (A) Distance open field | $F(2, 38) = 2.37$, $p = 0.11$ | $F(3, 38) = 0.43$, $p = 0.73$ | n.s |
| (B) Time center open field | $F(2, 38) = 0.92$, $p = 0.41$ | $F(3, 38) = 0.35$, $p = 0.79$ | n.s. |
| (C) Distance zero maze | $F(2, 38) = 3.43$, $p = 0.043$ | $F(3, 38) = 2.33$, $p = 0.08$ | n.s. |
| (D) Time open arms zero maze | $F(2, 38) = 1.56$, $p = 0.22$ | $F(3, 38) = 0.44$, $p = 0.72$ | n.s. |

TABLE 3

Two way ANOVA summary of statistics

| Parameter | Effect of treatment | Effect of cycle | Interaction |
|---|---|---|---|
| (A) % developed vesicles | $F(1, 32) = 10.15$, $p = 0.003$ | $F(3, 32) = 1.29$, $p = 0.31$ | n.s. |
| (B) Weight | $F(1, 32) = 2.36$, $p = 0.13$ | $F(3, 32) = 0.73$, $p = 0.54$ | n.s. |
| (C) Volume | $F(1, 32) = 2.44$, $p = 0.13$ | $F(3, 32) = 0.73$, $p = 0.53$ | n.s. |
| (D) Area | $F(1, 32) = 4.28$, $p = 0.04$ | $F(3, 32) = 0.72$, $p = 0.54$ | n.s. |

PUBLICATIONS CITED

These publications are incorporated by reference to the extent they relate materials and methods disclosed herein.

Torres-Reverón A, Khalid S, Williams T J, Waters E M, Drake C T, McEwen B S, Milner T A. *Ovarian steroids modulate leu-enkephalin levels and target leu-enkephalinergic profiles in the female hippocampal mossy fiber pathway.* Brain Res. 2008 Sep. 26; 1232:70-84. doi: 10.1016/j.brainres.2008.07.058.

Torres-Reverón A, Khalid S, Williams T J, Waters E M, Jacome L, Luine V N, Drake C T, McEwen B S, Milner T A. *Hippocampal dynorphin immunoreactivity increases in response to gonadal steroids and is positioned for direct modulation by ovarian steroid receptors.* Neuroscience. 2009 Mar. 3; 159(1):204-16. doi: 10.1016/j.neuroscience.2008.12.023.

Torres-Reverón A, Palermo K, Hernández-López A, Hernández S, Cruz M L, Thompson K J, Flores I, Appleyard C B. *Endometriosis Is Associated With a Shift in MU Opioid and NMDA Receptor Expression in the Brain Periaqueductal Gray.* Reprod Sci. 2016 September; 23(9):1158-67. doi: 10.1177/1933719116630410.

What is claimed is:

1. A method of treating endometriosis in a mammal in need thereof, said method comprising the step of administering a pharmaceutical composition comprising a corticotrophin releasing hormone (CRH) receptor antagonist to the mammal, wherein the CRH receptor antagonist is antalarmin, and wherein the administration is a parenteral administration or an oral administration.

2. The method of claim 1, wherein the pharmaceutical composition further comprises one or more agents selected from the group consisting of a surfactant, a stabilizer, a biomarker, a second active pharmaceutical ingredient (API), and combinations thereof.

3. The method of claim 1, wherein the pharmaceutical composition further comprises at least one excipient, a bioavailability-improving compound, at least one coating, or a combination thereof.

4. The method of claim 1, wherein the administration is given to the mammal for 7 days.

5. A method of treating a symptom associated with endometriosis in a mammal in need thereof, said method comprising the step of administering a corticotrophin releasing hormone (CRH) receptor antagonist to the mammal, wherein the CRH receptor antagonist is antalarmin, and wherein the administration is a parenteral administration or an oral administration.

6. The method of claim 5, wherein the symptom associated with endometriosis is reduction of endometriotic vesicle size.

7. The method of claim 5, wherein the symptom associated with endometriosis is inflammation.

8. A method of reducing lesion enlargement associated with endometriosis in a mammal in need thereof, said method comprising the step of administering a corticotrophin releasing hormone (CRH) receptor antagonist to the mammal, wherein the CRH receptor antagonist is antalarmin, and wherein the administration is a parenteral administration or an oral administration.

9. The method of claim 8, wherein the lesion is an endometriotic vesicle.

10. The method of claim 8, wherein the lesion is a cyst.

11. The method of claim 8, wherein the cyst is an ovarian cyst.

12. The method of claim 1, wherein the administration is a parenteral administration.

13. The method of claim 12, wherein the parenteral administration is selected from the group consisting of an intravenous administration, an intramuscular administration, and a subcutaneous administration.

14. The method of claim 1, wherein the administration is an oral administration.

15. The method of claim 5, wherein the administration is a parenteral administration.

16. The method of claim 15, wherein the parenteral administration is selected from the group consisting of an intravenous administration, an intramuscular administration, and a subcutaneous administration.

17. The method of claim 5, wherein the administration is an oral administration.

18. The method of claim 8, wherein the administration is a parenteral administration.

19. The method of claim 18, wherein the parenteral administration is selected from the group consisting of an intravenous administration, an intramuscular administration, and a subcutaneous administration.

20. The method of claim 8, wherein the administration is an oral administration.

* * * * *